(12) United States Patent
Ahmed et al.

(10) Patent No.: US 11,807,617 B2
(45) Date of Patent: Nov. 7, 2023

(54) HIGHLY EFFICIENT SYNTHESIS OF Z-MACROCYCLES USING STEREORETENTIVE, RUTHENIUM-BASED METATHESIS CATALYSTS

(71) Applicant: CALIFORNIA INSTITUTE OF TECHNOLOGY, Pasadena, CA (US)

(72) Inventors: Tonia S. Ahmed, Pasadena, CA (US); Robert H. Grubbs, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 127 days.

(21) Appl. No.: 17/336,756

(22) Filed: Jun. 2, 2021

(65) Prior Publication Data

US 2021/0355099 A1 Nov. 18, 2021

Related U.S. Application Data

(63) Continuation of application No. 16/611,329, filed as application No. PCT/US2018/029106 on Apr. 24, 2018, now Pat. No. 11,053,209.

(Continued)

(51) Int. Cl.
*C07D 313/00* (2006.01)
*B01J 31/22* (2006.01)

(52) U.S. Cl.
CPC .......... *C07D 313/00* (2013.01); *B01J 31/226* (2013.01); *B01J 31/2273* (2013.01);
(Continued)

(58) Field of Classification Search
CPC ... C07D 313/00; B01J 31/226; B01J 31/2273; B01J 31/2291; B01J 2231/543;
(Continued)

(56) References Cited

U.S. PATENT DOCUMENTS 9,586,981 B2    3/2017  Rosebrugh et al.
2012/0323000 A1  12/2012  Hoveyda et al.
2016/0101414 A1  4/2016  Hartung et al.

FOREIGN PATENT DOCUMENTS

CN          104854119 A      8/2015

OTHER PUBLICATIONS

Marx et al., "Stereoselective Access to Z and E Macrocycles by Ruthenium-Catalyzed Z-Selective Ring-Closing Metathesis and Ethenolysis", JACS 135(1):94-97 (2013).
(Continued)

*Primary Examiner* — Taylor V Oh
(74) *Attorney, Agent, or Firm* — RAPHAEL BELLUM PLLC

(57) ABSTRACT

A highly efficient, Z-selective ring-closing metathesis system for the formation of macrocycles using a stereoretentive, ruthenium-based catalyst supported by a dithiolate ligand is reported. This catalyst is demonstrated to be remarkably active as observed in initiation experiments showing complete catalyst initiation at −20° C. within 10 min. Using easily accessible diene starting materials bearing a Z-olefin moiety, macrocyclization reactions generated products with significantly higher Z-selectivity in appreciably shorter reaction times, in higher yield, and with much lower catalyst loadings than in previously reported systems. Macrocyclic lactones ranging in size from twelve-membered to seventeen-membered rings are synthesized in moderate to high yields (68-79% yield) with excellent Z-selectivity (95%-99% Z).

2 Claims, 5 Drawing Sheets

1

2

Ar = 2,4,6-triisopropylphenyl
3

4

Related U.S. Application Data

(60) Provisional application No. 62/521,647, filed on Jun. 19, 2017, provisional application No. 62/503,155, filed on May 8, 2017.

(52) U.S. Cl.
CPC ...... *B01J 31/2291* (2013.01); *B01J 2231/543* (2013.01); *B01J 2531/821* (2013.01)

(58) Field of Classification Search
CPC ................ B01J 2531/821; B01J 31/181; B01J 31/1825; B01J 2540/20; B01J 2540/22; B01J 2540/225; B01J 2540/34; B01J 2540/40; B01J 2540/62; B01J 31/2208; B01J 31/2278; C08F 132/08
USPC ........................................................ 549/266
See application file for complete search history.

(56) References Cited

OTHER PUBLICATIONS

International Search Report and Written Opinion in International Application No. PCT/US2018/029106, dated Aug. 8, 2018.
International Preliminary Report on Patentability in International Application No. PCT/US2018/029106, dated Nov. 21, 2019.
Koh et al., "High-value alcohols and higher-oxidation-state compounds by catalytic Z-selective cross-metathesis", Nature, Jan. 8, 2015, vol. 517, No. 7533, pp. 181-186.
Ahmed; Grubbs Angew. Chem. Int. Ed., Jul. 12, 2017, 56, 11213-11216, XP055575691.
Xu et al., J.Am.Chem. Soc., Jul. 27, 2017, 139, 10919-10928, XP0555756.
Grisi et al., "Synthesis of Unsaturated Macrocycles by Ru-Catalyzed Ring-Closing Metathesis: A Comparative Study", European Journal of Organic Chemistry, 2012, 30, 5928-5934.

HIGHLY EFFICIENT SYNTHESIS OF Z-MACROCYCLES USING STEREORETENTIVE, RUTHENIUM-BASED METATHESIS CATALYSTS

RELATED APPLICATIONS

This application is a Continuation of application Ser. No. 16/611,329, filed Nov. 6, 2019; which is a national stage of PCT International Application No. PCT/US2018/029106, filed Apr. 24, 2018; which claims the benefit of U.S. Provisional Patent Application No. 62/503,155 filed May 8, 2017 and the benefit of U.S. Provisional Patent Application No. 62/521,647 filed Jun. 19, 2017, the contents of which are incorporated herein by reference in their entirety.

STATEMENT OF FEDERAL SUPPORT

This invention was made with government support under grant number GM031332 awarded by the National Institutes of Health, grant number CHE1502616 awarded by the National Science Foundation and grant number N00014-14-1-0650 awarded by the Office of Naval Research. The government has certain rights in the invention.

TECHNICAL FIELD

This invention relates generally to the use of Ruthenium based metathesis catalysts in the synthesis of metathesis of olefins and olefin compounds, more particularly, in the use of such catalysts in the synthesis of Z-macrocycles. The invention has utility in the fields of organic synthesis, pharmaceutical industry as well as in flavors and fragrances.

A highly efficient, Z-selective ring-closing metathesis system for the formation of macrocycles using a stereoretentive, ruthenium-based catalyst supported by a dithiolate ligand is reported. This catalyst is demonstrated to be remarkably active as observed in initiation experiments showing complete catalyst initiation at −20° C. within 10 min. Using easily accessible diene starting materials bearing a Z-olefin moiety, macrocyclization reactions generated products with significantly higher Z-selectivity in appreciably shorter reaction times, in higher yield, and with much lower catalyst loadings than in previously reported systems. Macrocyclic lactones ranging in size from twelve-membered to seventeen-membered rings are synthesized in moderate to high yields (68-79% yield) with excellent Z-selectivity (95%-99% Z).

BACKGROUND

Transition-metal catalyzed ring-closing metathesis (RCM) has become a powerful method for generating cyclic molecules (Grubbs, R. H., Wenzel, A. G., O'Leary, D. J., Khosravi, E., Eds. *Handbook of Metathesis*; Wiley-VCH: Weinheim, 2015).

It is used widely in the synthesis of several pharmaceuticals as well as in the production of pheromones and musks, as replacements for toxic synthetic polycyclic and nitroarene musks [(a) Michrowska, A.; Wawrzyniak, P.; Grela, K. *Eur. J. Org. Chem.* 2004, 2053. (b) Rimkus, G. G. The Handbook of Environmental Chemistry; Springer: Berlin, 2004; Vol. 3X. (c) Rowe, D. J. Chemistry and Technology of Flavors and Fragrances; Blackwell: Oxford, U. K., 2005. (d) Gradillas, A.; Perez-Castells, J. *Angew. Chem., Int. Ed.* 2006, 45, 6086. (e) Ohloff, G.; Pickenhagen, W.; Kraft, P. Scent and Chemistry: The Molecular World of Odors; Verlag Helvetica Acta: Zuirich, 2011. (f) Marx, V. M.; Herbert, M. B.; Keitz, B. K.; Grubbs, R. H. *J. Am. Chem. Soc.* 2013, 135, 94. (g) Higman, C. S.; Lummiss, J. A. M.; Fogg, D. E. *Angew. Chem., Int. Ed.* 2016, 55, 3552].

The stereochemistry of the alkene, E- or Z-, in these cyclic structures is often crucial to the biological activity of a molecule or its olfactory characteristics, and small amounts of impurity of the other stereoisomer in chemical mixtures, can drastically decrease their potency. It is often particularly difficult to separate E- and Z-isomers as techniques for their separation are not general. As such, methods for producing stereochemically pure cyclic compounds are of paramount importance.

Controlling olefin stereochemistry in RCM reactions can be difficult. When using common non-selective metathesis catalysts, selectivity is controlled by the thermodynamic stability of the olefin products and can vary depending on ring size and double bond position [(a) Fürstner, A.; Langemann, K. *J. Org. Chem.* 1996, 61, 3942. (b) Fürstner, A.; Langemann, K. *Synthesis* 1997, 792. (c) Goldberg, W. P. D.; Hobber, A. S.; Weiler, L. *Tetrahedron Lett.* 1998, 39, 4955. (d) Lee, C. W.; Grubbs, R. H. *Org. Lett.,* 2000, 2 (14), 2145. (e) Yu, M.; Wang, C.; Kyle, A. F.; Jakubec, P.; Dixon, D. J.; Schrock, R. R.; Hoveyda, A. H. *Nature* 2011, 479, 88].

Furthermore, high catalyst loadings are often needed for macrocyclization reactions using RCM. In these instances, removal of residual metals, the presence of which can be undesirable in the end product or could potentially isomerize products, can be difficult. For some applications, this requires further purification with lead tetra acetate or phosphine additives or with multiple chromatographic columns followed by treatment with charcoal [(a) Paquette, L. A.; Schloss, J. D.; Efremov, I.; Fabris, F.; Gallou, F.; Mendez-Andino, J.; Yang, J. *Org. Lett.* 2000, 2, 1259. (b) Maynard, H.; Grubbs, R. H. *Tetrahedron Lett.* 1999, 40, 4137]. Reducing catalyst loadings required for these reactions is thus an important goal.

One established method for stereoselectively generating Z-macrocycles is ring-closing alkyne metathesis followed by Lindlar hydrogenation [(a) Fürstner, A.; Mathes, C.; Lehmann, C. W. *Chem. Eur. J.* 2001, 7, 5299. (b) Nilson, M. G. & Funk, R. L. *Org. Lett.* 2010, 12, 4912]. Z-macrocycles have also been synthesized by reaction of terminal olefins with internal vinyl silanes followed by protodesilylation (Wang, Y.; Jimenez, M.; Hansen, A. S.; Raiber, E.-A.; Schreiber, S. L.; Young, D. W. *J. Am. Chem. Soc.* 2011, 133, 9196). However, these approaches require multiple steps to synthesize the desired product, and thus more direct methods using olefin metathesis are desirable. In 2011, the first report of Z-selective RCM was disclosed. Mo- and W-based catalysts 1-3 of FIG. 1, were used to synthesize a sixteen-membered macrocyclic lactone (91-95% Z), nakadomarin A (90-97% Z), and epothilone C (69-97% Z) (Yu, M.; Wang, C.; Kyle, A. F.; Jakubec, P.; Dixon, D. J.; Schrock, R. R.; Hoveyda, A. H. *Nature* 2011, 479, 88). While these catalysts afforded exceptional selectivity, they required catalyst loadings of catalyst 5 to 6 mol %. One year later, Z-selective cyclometallated ruthenium-based catalyst 4 of FIG. 1 (7.5 mol %) was reported to generate macrocyclic lactones, lactams and ketones (75-94% Z) with the purpose of synthesizing pheromones and fragrances (Marx, V. M.; Herbert, M. B.; Keitz, B. K.; Grubbs, R. H. *J. Am. Chem. Soc.* 2013, 135, 94; Herbert, M. B.; Marx, V. M.; Pederson R. L.; Grubbs, R. H. *A.C.I.E.* 2013, 52, 310). This method was limited by long reaction times, required the use of high boiling solvents and elevated temperatures, and delivered most products with generally ca. 85% Z-selectivity.

BRIEF DESCRIPTION OF THE FIGURES

FIG. 3A shows proposed disfavored and favored metallacyclobutane intermediates in macrocyclization reactions implementing stereoretentive catalyst 5. FIG. 3B shows synthesis of diene substrates from acyl chlorides and Z-hydroxy olefins.

FIG. 4A shows the reaction of catalyst 5 with butyl vinyl ether. FIG. 4B shows the plot of ln([Ru]/[Ru]$_0$) versus time for initiation experiments conducted with catalysts 4 and 5 at 0° C. and −20° C. monitored by disappearance of the benzylidene signal by $^1$H NMR. Plots remain approximately linear for three half-lives of the reaction.

SUMMARY

Figure 1:
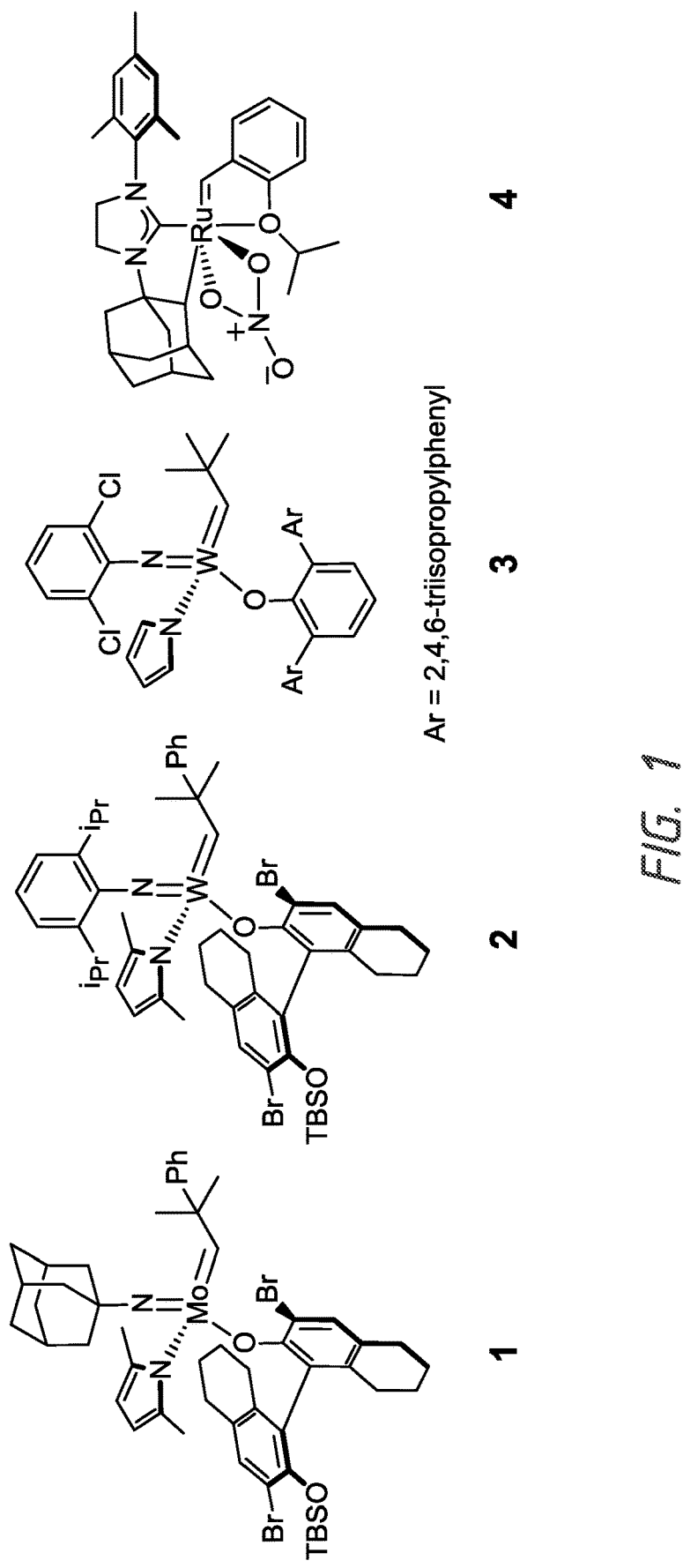
FIG. 1. Catalysts used previously to selectively generate highly Z-macrocycles.
Figure 2:
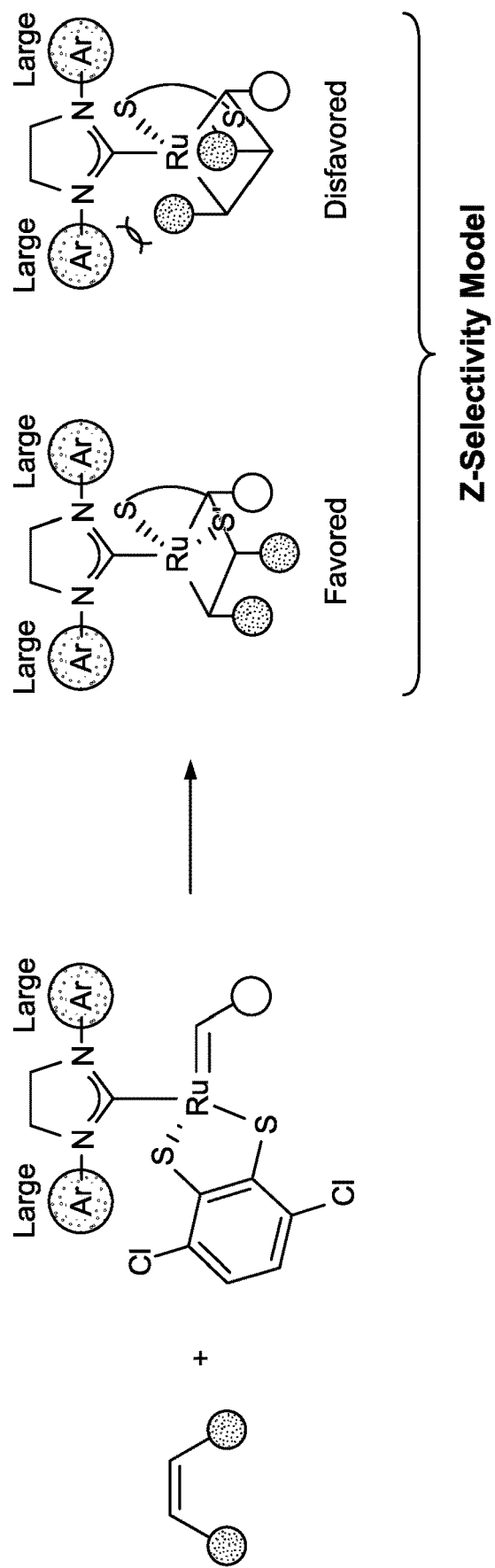
FIG. 2. Model for Z-selectivity using stereoretentive metathesis catalysts in cross-metathesis.

In 2016, the first demonstration of high stereoretention in transition metal-catalyzed olefin metathesis was reported (Johns, A. M.; Ahmed, T. S.; Jackson, B. W.; Grubbs, R. H.; Pederson, R. L. *Org. Lett.* 2016, 18 (4), 772). Using Ru catalysts supported by dithiolate ligands, cross metathesis between two Z-olefins or between a Z-olefin and a terminal olefin generated products with high Z-selectivity (>96% Z) (Koh, M. J.; Khan, R. K. M.; Torker, S.; Yu, M.; Mikus, M. S.; Hoveyda, A. H. *Nature* 2015, 517, 181). Conversely, cross metathesis between two E-olefins or between an E-olefin and a terminal olefin, generated products with kinetic E-selectivity (>98% E). The proposed model for Z-selectivity is based on a proposed side-bound metallacyclobutane intermediate in which stereoselectivity arises from the α-substituents of the metallacyclobutane favorably pointing down, away from the two large N-aryl groups of the N-heterocyclic carbene ligand (FIG. 2). Given that the reacting olefin has Z-stereochemistry, the β-substituent points down in the favored proposed intermediate. Subsequent cycloreversion of this metallocyclobutane intermediate leads to the formation of the Z-product.

Figures 3A, 3B:
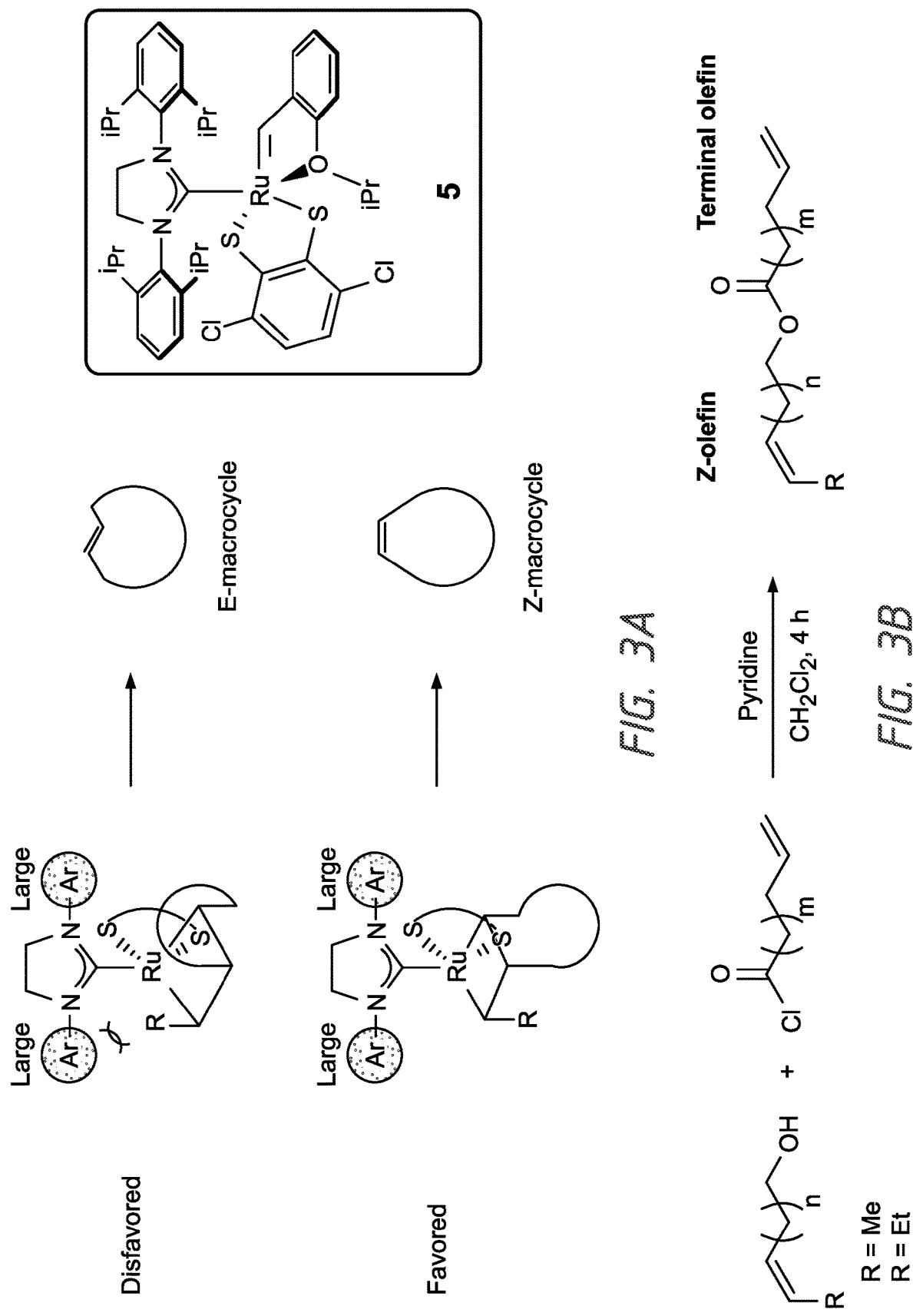
FIGS. 3A-3B.

Based on this model for selectivity, it was expected that highly Z-selective RCM to generate Z-macrocycles could be possible from diene substrates containing a Z-olefin and a terminal olefin using these catalysts (FIG. 3A). These substrates are easily synthesized in high yield by reaction of commercially available Z-hydroxy olefins with alkenoyl chlorides (FIG. 3B). Substrates were designed such that RCM of these substrates would give the desired product as well as a gaseous byproduct, propylene or 1-butene, which could be readily removed from the reaction mixture.

Figure 4A:
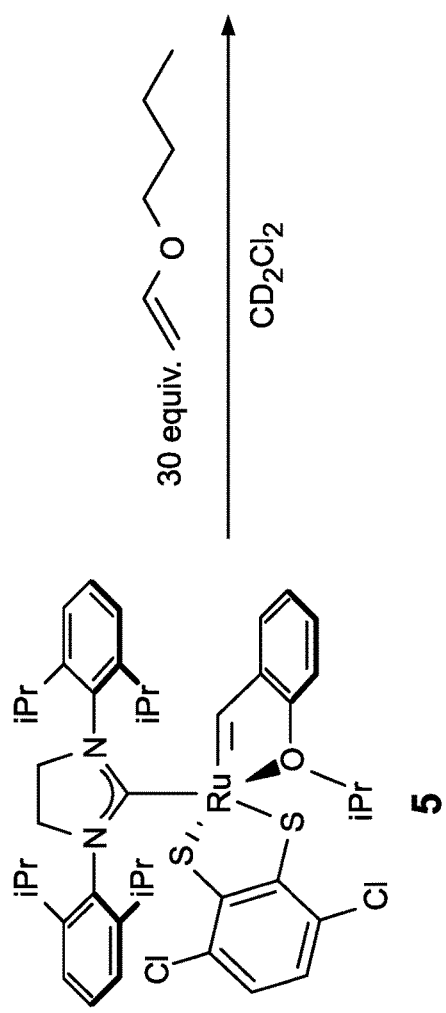
FIGS. 4A-4B.
Figure 4A:
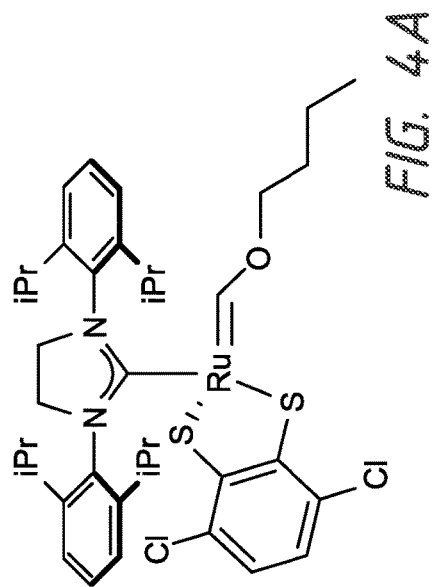
Figure 4B:
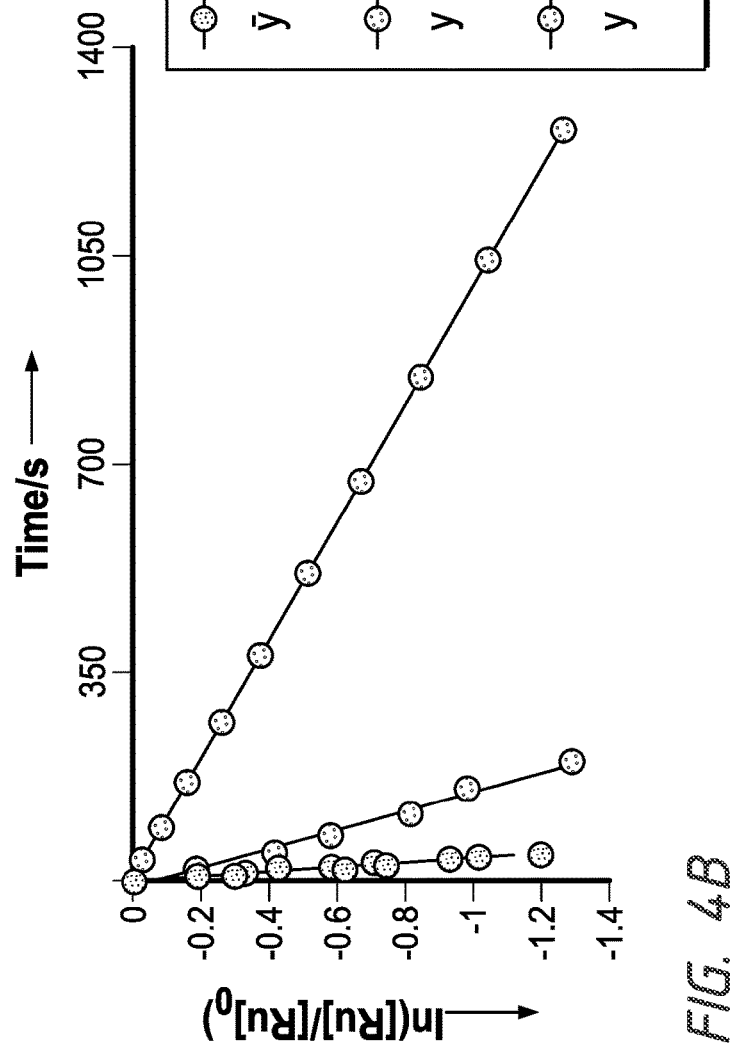
Figure 5:
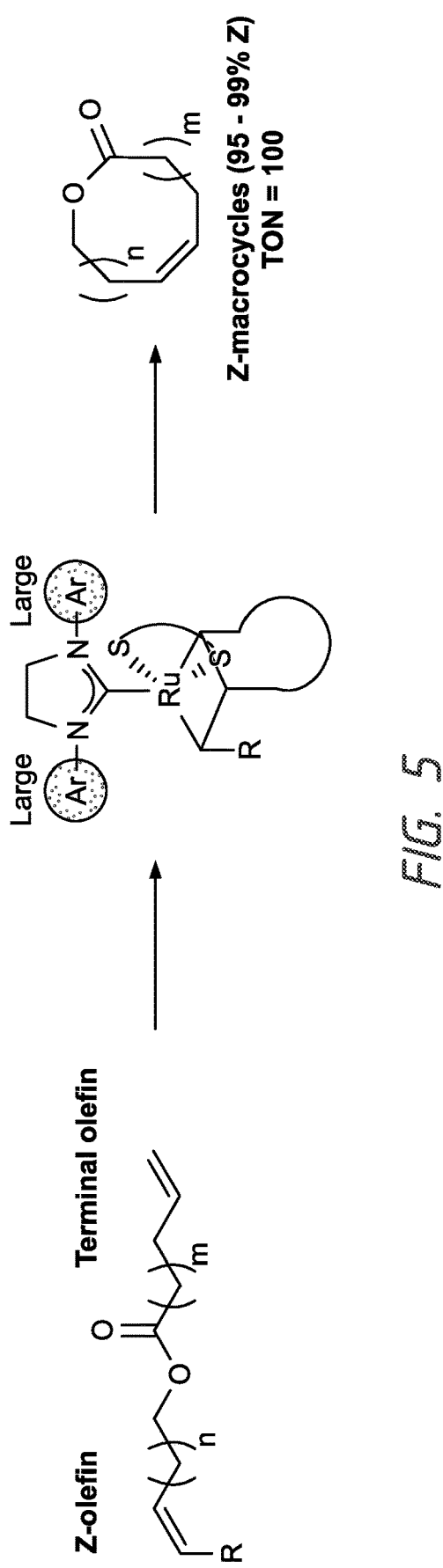
FIG. 5. Proposed favored metallacyclobutane intermediate in macrocylization reaction of Z-olefin with a terminal olefin leading to Z-macrocycles with 95-99% Z-selectivity.

For these reactions, catalyst 5, bearing an NHC with N-2,6-di-iso-propylphenyl groups, was chosen due to its remarkable activity in cross-metathesis reactions of Z-olefins. To compare the initiation rates of catalyst 4 and catalyst 5, the reactions of butyl vinyl ether with each catalyst were monitored using $^1$H NMR experiments (FIGS. 4A and 4B). Under standard conditions at 30° C., catalyst 5 had already fully initiated within the 15 s required to acquire the first spectrum, and thus a rate constant could not be determined (Keitz, B.; Endo, K.; Patel, P. R. Herbert, M. B.; Grubbs, R. H. *J. Am. Chem. Soc.*, 2012, 134 (1), 693). The reaction was then monitored at 0° C. and was completed within 2 min with catalyst 5 while catalyst 4 required 1.5 h. Values of k$_{init}$ for catalyst 4 and catalyst 5 at this temperature were determined to be 1.00×10$^{-3}$ s$^{-1}$ and 2.42×10$^{-2}$ s$^{-1}$, respectively. Thus, there is a magnitude of difference in the initiation rates of these catalysts, k$_{rel}$=k$_{init5}$/k$_{init4}$=24.2. Furthermore, full initiation of catalyst 5 was remarkably complete at −20° C. within 10 min with k$_{init}$=6.14×10$^{-3}$ s$^{-1}$. Negligible Fischer carbene formation could be observed using catalyst 4 at −20° C. This stark difference in initiation rate is a direct reflection of the significantly greater activity of 5 compared to catalyst 4.

RCM was then attempted using catalyst 5 and was shown to be possible using a variety of substrates, (6)-(12) (Table 1). Using a standard catalyst loading of 6 mol % often used in macrocyclization reactions, reactions were completed within 1 h in dichloromethane under static vacuum (30 mTorr) at 40° C. Twelve-membered to seventeen-membered rings were all synthesized with high Z-selectivity (95-99% Z) in moderate to high yields (68-79% isolated yield). Yuzu lactone, (Z-7), is in high demand by the perfume industry and can be synthesized more rapidly and selectively using catalyst 5 than in previous reports. Larger macrocyclic lactones, fifteen-membered to seventeen-membered rings, were synthesized in slightly higher yields than with smaller twelve-membered to fourteen-membered rings.

TABLE 1
Synthesis of macrocycles using Catalyst 5.
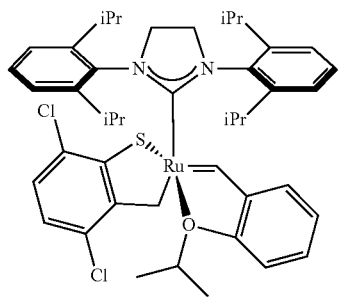
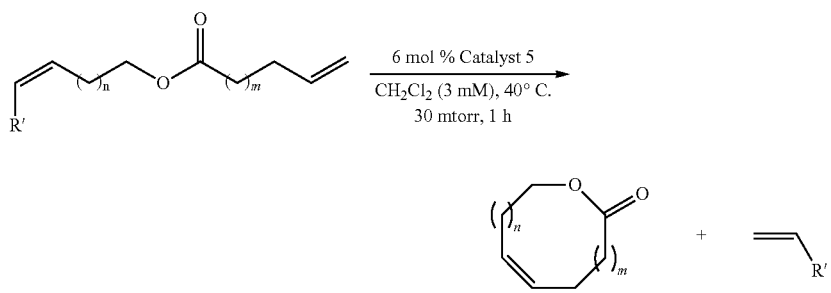
| Entry | Substrate | Product | Yield [a] | Z/E [b] |
|---|---|---|---|---|
| 1 | (6) | (Z-6) 12 | 70% | >99/1 |
| 2 | (7) | (Z-7) 13 | 68% | 95/5 |
| 3 | (8) | (Z-8) 14 | 67% | 95/5 |

TABLE 1-continued
Synthesis of macrocycles using Catalyst 5.
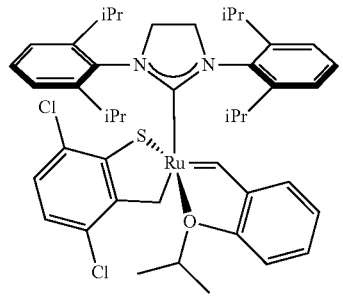
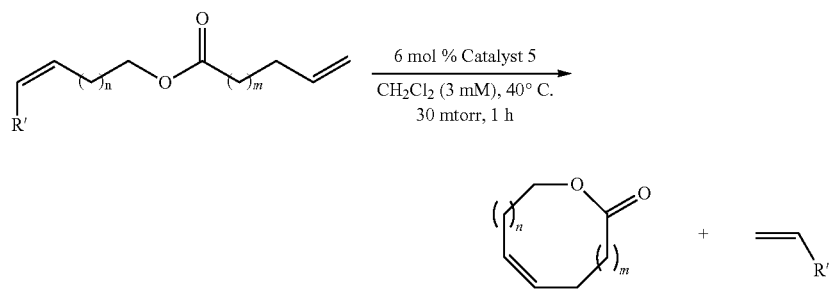
| Entry | Substrate | Product | Yield[a] | Z/E[b] |
|---|---|---|---|---|
| 4 | (9) | (Z-9) 14 | 72% | 98/2 |
| 5 | (10) | (Z-10) 15 | 74% | 99/1 |
| 6 | (11) | (Z-11) 16 | 79% | 95/5 |

TABLE 1-continued

Synthesis of macrocycles using Catalyst 5.

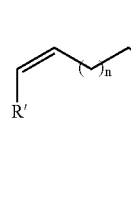

| Entry | Substrate | Product | Yield [a] | Z/E [b] |
|---|---|---|---|---|
| 7 | (12) | (Z-12) | 75% | 95/5 |

[a] Isolated yields.
[b] Selectivity determined by gas chromatography. Selectivities of Z-7 and Z-8 were determined by $^1$H NMR.

Given the exceptional activity exhibited by catalyst 5 in initiation experiments and its high activity in macrocyclic RCM (TON of 11-13 were achieved using 6 mol % catalyst loading), the limit for the catalyst loading required for reaction was examined. Using 0.5 mol % 5, TON of 100 were attained in the macrocyclization of (8) within 1 h as determined by observation of aliquots of the reaction by $^1$H NMR. With 1 mol % catalyst 5, complete conversion of the starting material to the macrocyclic product and a small amount of unidentified byproduct, possibly an oligomer of the starting material, was observed. This is significantly lower than reported catalyst loadings, used for achieving high conversion in previously reported Z-selective macrocyclizations.

In summary, highly active, stereoretentive Ru-based catalyst 5 was used for generating highly Z-macrocycles (95-99% Z) from easily available diene substrates with a Z-olefin moiety. The exceptional activity exhibited by this catalyst was determined through initiation studies and showed that full catalyst initiation could be achieved at −20° C. within minutes. Twelve-membered to seventeen-membered macrocycles including yuzu lactone were synthesized using this method in moderate to high yields (67-79% yield). These reactions were completed in significantly shorter times and using lower catalyst loadings than in previously reported Z-selective systems was shown to be possible with TON of up to 100. Further studies using stereoretention for E-selective macrocyclization are underway.

In another embodiment the invention provides a method for generating Z-macrocycles via macrocyclic ring-closing metathesis of diene substrate bearing a Z-olefin moiety in the presence of a stereoretentive Ru-based catalyst of Formula (I):

Formula (I)

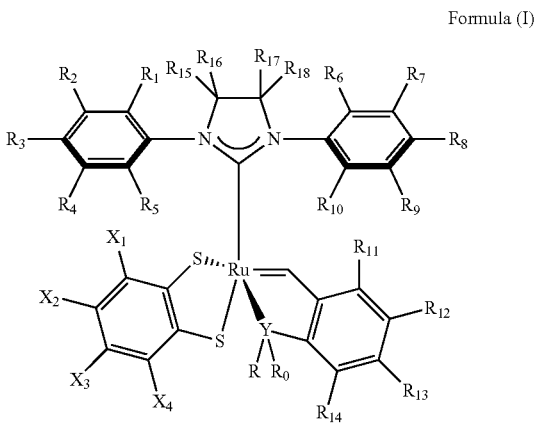

wherein:

R and $R_0$ are independently nil, H, methyl, ethyl, propyl, iso-propyl, butyl, sec-butyl, tert-butyl, or phenyl;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, iso-propoxy, butyl, sec-butyl, tert-butyl, phenyl, fluoro, chloro, bromo, iodo, nitro, dimethylaminosulfonate, diethylaminosulfonate, or cyano;

$R_{15}$, $R_{16}$, $R_{17}$, and $R_{18}$ are independently H or methyl;

$X_1$, $X_2$, $X_3$, and $X_4$ are independently H, fluoro, chloro, bromo, iodo, methyl, ethyl, propyl, iso-propyl, butyl, sec-butyl, tert-butyl, or phenyl; and Y is oxygen, sulfur, nitrogen, or iodo.

In another embodiment the invention provides a method for generating Z-macrocycles via macrocyclic ring-closing metathesis of diene substrate bearing a Z-olefin moiety in the presence of a stereoretentive Ru-based catalyst of Formula (II):

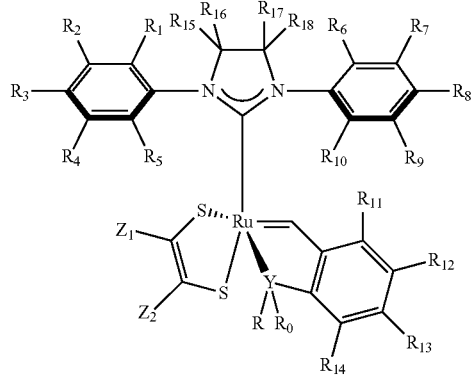

Formula (II)

wherein:

R and $R_0$ are independently nil, H, methyl, ethyl, propyl, iso-propyl, butyl, sec-butyl, tert-butyl, or phenyl;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano;

$R_{15}$, $R_{16}$, $R_{17}$, and $R_{18}$ are independently H or methyl;

$Z_1$ and $Z_2$ are independently cyano or nitro; and

Y is oxygen, sulfur, nitrogen, or iodo.

DETAILED DESCRIPTION

Terminology and Definitions

Unless otherwise indicated, the invention is not limited to specific reactants, reaction conditions, or the like, as such may vary. It is also to be understood that the terminology used herein is for the purpose of describing particular embodiments and is not to be interpreted as being limiting.

As used in the specification and the appended claims, the singular forms "a," "an," and "the" include plural referents unless the context clearly dictates otherwise. Thus, for example, reference to "an olefin" includes a single olefin as well as a combination or mixture of two or more olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention and are not meant to be limiting in any fashion.

In this specification and in the claims that follow, reference will be made to a number of terms, which shall be defined to have the following meanings.

The term "diene bearing a Z-olefin moiety" or "diene with a Z-olefin moiety" as used herein means an unsaturated hydrocarbon containing two double bonds wherein one of them is an internal double bond in the Z-configuration.

The term "product internal olefin" as used herein means an internal olefin present in a ring-closing metathesis product formed by a ring-closing metathesis reaction, wherein each of the olefinic carbons (i.e., the carbons of the carbon-carbon double bond) of the internal olefin may have an E-configuration or a Z-configuration.

The term "nil," as used herein, means absent or nonexistent.

The term "methyl," as used herein, represents a group of formula "—$CH_3$."

The term "ethyl," as used herein, represents a group of formula "—$CH_2CH_3$."

The term "propyl," as used herein, represents a group of formula "—$CH_2CH_2CH_3$."

The term "iso-propyl," as used herein, represents a group of formula "—$CH(CH_3)_2$."

The term "iso-propoxy," as used herein, represents a group of formula "—$OCH(CH_3)_2$."

The term "butyl," as used herein, represents a group of formula "—$CH_2CH_2CH_2CH_3$."

The term "sec-butyl," as used herein, represents a group of formula "—$CH(CH_3)(CH_2CH_3)$."

The term "tert-butyl," as used herein, represents a group of formula "—$CH(CH_3)_2$."

The term "phenyl," as used herein, represents a group of formula "—$C_6H_5$."

The term "fluoro," as used herein, represents a group of formula "—F."

The term "chloro," as used herein, represents a group of formula "—Cl."

The term "bromo," as used herein, represents a group of formula "—Br."

The term "iodo," as used herein, represents a group of formula "—I."

The term "nitro," as used herein, represents a group of formula "—$NO_2$."

The term "dimethylaminosulfonate," as used herein, represents a group of formula "—$NHSO_2Me_2$."

The term "diethylaminosulfonate," as used herein, represents a group of formula "—$NHSO_2Et_2$."

The term "cyano," as used herein, represents a group of formula "—C≡N."

The formula "O," as used herein, represents an oxygen atom.

The formula "N," as used herein, represents a nitrogen atom.

The formula "S," as used herein, represents a sulfur atom.

The formula "H," as used herein, represents a hydrogen atom.

Stereoretentive Ru-Based Catalysts

The invention provides a method for generating Z-macrocycles via macrocyclic ring-closing metathesis of diene substrate bearing a Z-olefin moiety in the presence of a stereoretentive Ru-based catalyst of Formula (I):

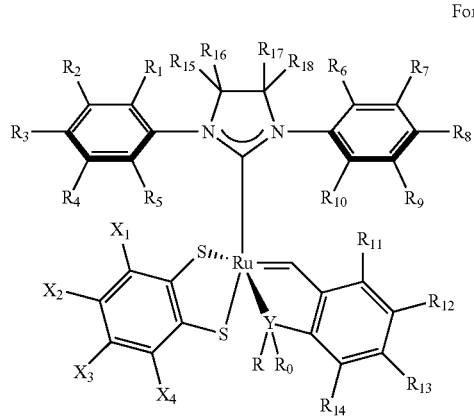

Formula (I)

wherein:
R and $R_0$ are independently nil, H, methyl, ethyl, propyl, iso-propyl, butyl, sec-butyl, tert-butyl, or phenyl;
$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, iso-propoxy, butyl, sec-butyl, tert-butyl, phenyl, fluoro, chloro, bromo, iodo, nitro, dimethylaminosulfonate, diethylaminosulfonate, or cyano;
$R_{15}$, $R_{16}$, $R_{17}$, and $R_{18}$ are independently H or methyl;
$X_1$, $X_2$, $X_3$, and $X_4$ are independently H, fluoro, chloro, bromo, iodo, methyl, ethyl, propyl, iso-propyl, butyl, sec-butyl, tert-butyl, or phenyl; and
Y is oxygen, sulfur, nitrogen, or iodo.

In another embodiment the invention provides a method for generating Z-macrocycles via macrocyclic ring-closing metathesis of diene substrate with a Z-olefin moiety in the presence of a stereoretentive Ru-based catalyst of Formula (I), wherein:
R is nil, iso-propyl, or butyl;
$R_0$ is nil;
$R_1$, $R_2$, $R_3$, $R_4$, $R_5$, $R_6$, $R_7$, $R_8$, $R_9$, and $R_{10}$ are independently H, methyl, iso-propyl, or fluoro;
$R_{11}$, $R_{12}$, $R_{13}$, and $R_{14}$ are independently H, phenyl, iso-propoxy, nitro, diethylaminosulfonate, or dimethylaminosulfonate;
$R_{15}$, $R_{16}$, $R_{17}$, and $R_{18}$ are independently H or methyl;
$X_1$, $X_2$, $X_3$, and $X_4$ are independently H, fluoro, or chloro; and
Y is oxygen, sulfur, or iodo.

In another embodiment the invention provides a method for generating Z-macrocycles via macrocyclic ring-closing metathesis of diene substrate bearing a Z-olefin moiety in the presence of a stereoretentive Ru-based catalyst of Formula (I), wherein:
R is nil, iso-propyl, or tert-butyl;
$R_0$ is nil;
$R_1$ is methyl, iso-propyl, or fluoro;
$R_2$ is H or methyl;
$R_3$ is H or methyl;
$R_4$ is H or methyl;
$R_5$, is H, methyl, iso-propyl, or fluoro;
$R_6$ is methyl, iso-propyl, or fluoro;
$R_7$ is H or methyl;
$R_8$ is H or methyl;
$R_9$ is H or methyl;
$R_{10}$ is H, methyl, iso-propyl, or fluoro;
$R_{11}$ is H;
$R_{12}$ is H;
$R_{13}$ is H, nitro, iso-propoxy, diethylaminosulfonate, or dimethylaminosulfonate;
$R_{14}$ is H or phenyl;
$R_{15}$ is H or methyl;
$R_{16}$ is H or methyl;
$R_{17}$ is H or methyl;
$R_{18}$ is H or methyl;
$X_1$ is H, fluoro, or chloro;
$X_2$ is H or fluoro;
$X_3$ is H or fluoro;
$X_4$ is H, fluoro, or chloro; and
Y is oxygen, sulfur, or iodo.

In another embodiment the invention provides a method for generating Z-macrocycles via macrocyclic ring-closing metathesis of a diene substrate bearing a Z-olefin moiety in the presence of a stereoretentive Ru-based catalyst of Formula (I), wherein the stereoretentive Ru-based catalyst is selected from:

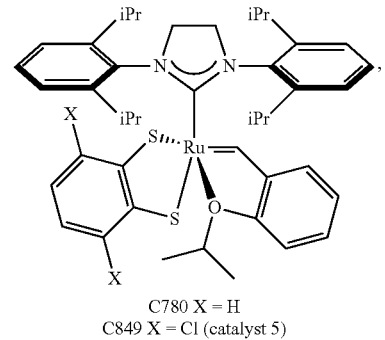

C780 X = H
C849 X = Cl (catalyst 5)

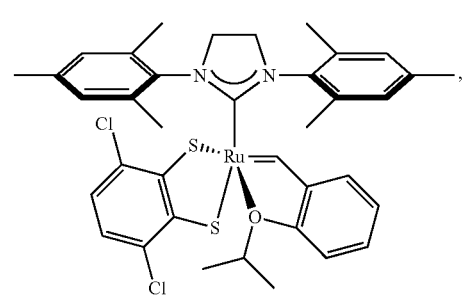

C765

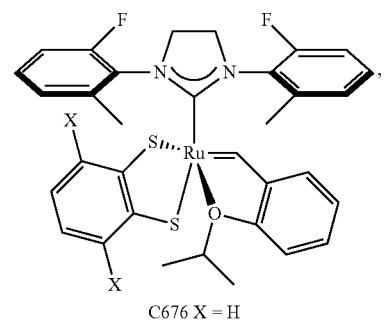

C676 X = H
C745 X = Cl

-continued
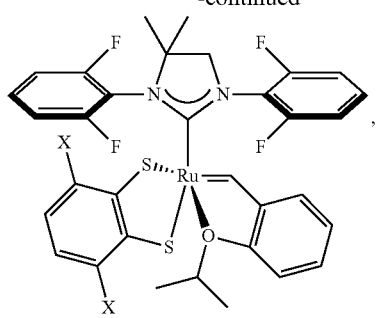
C712f X = H
C781 X = Cl
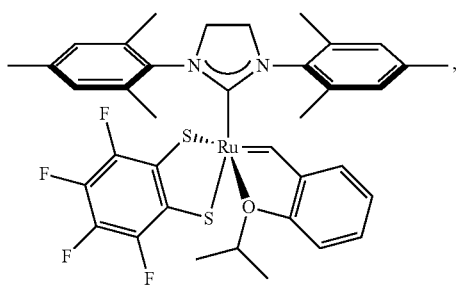
C768
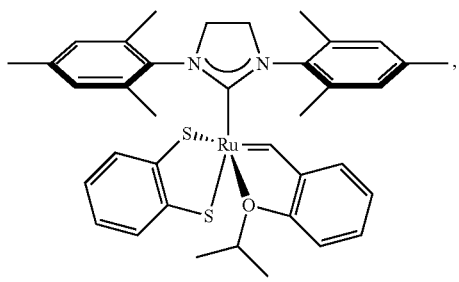
C696
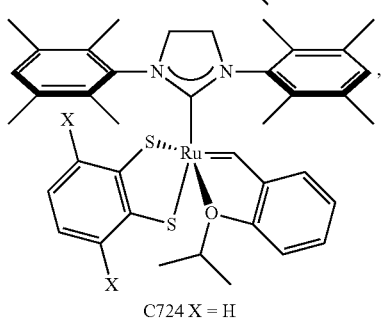
C724 X = H
C793 X = Cl
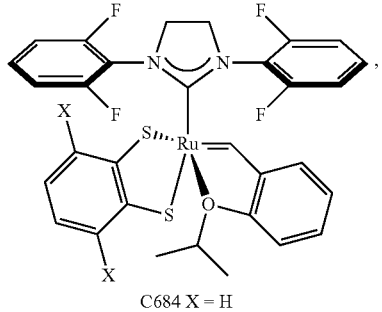
C684 X = H
C752 X = Cl
-continued
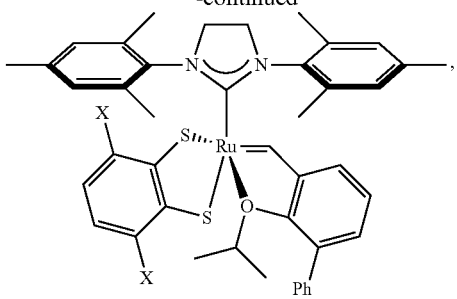
C772 X = H
C841 X = Cl
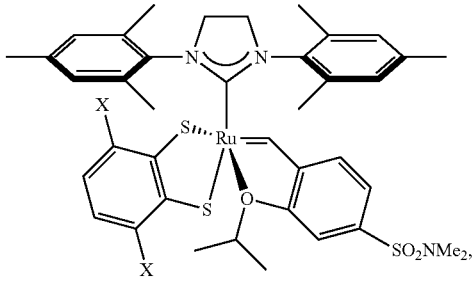
C803 X = H
C872 X = Cl
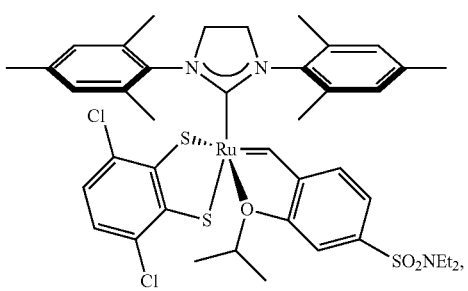
C832 X = H
C901 X = Cl
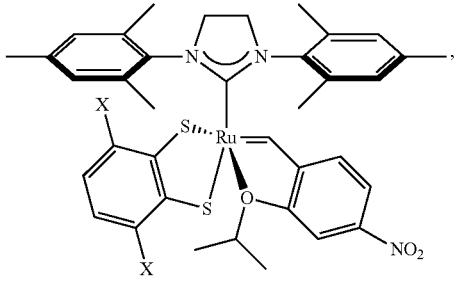
C741 X = H
C810 X = Cl
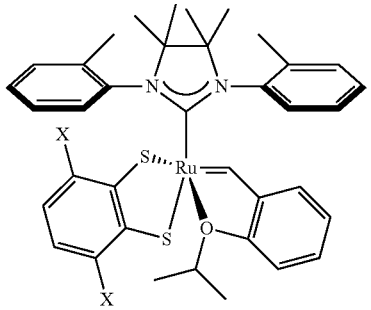
C696h X = H
C765 X = Cl -continued
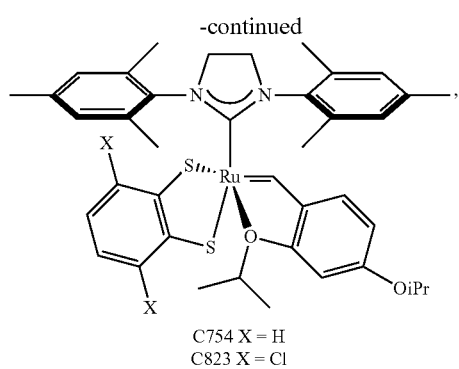
C754 X = H
C823 X = Cl
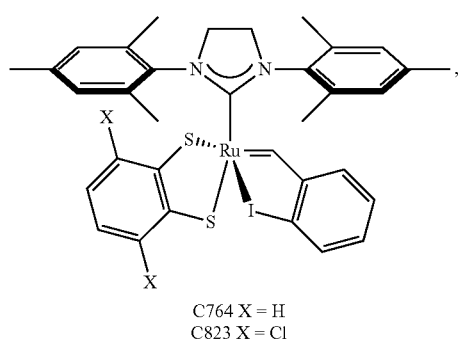
C764 X = H
C823 X = Cl
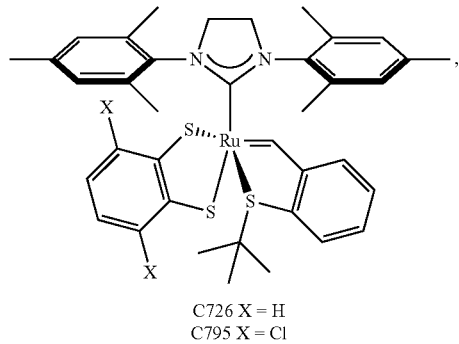
C726 X = H
C795 X = Cl
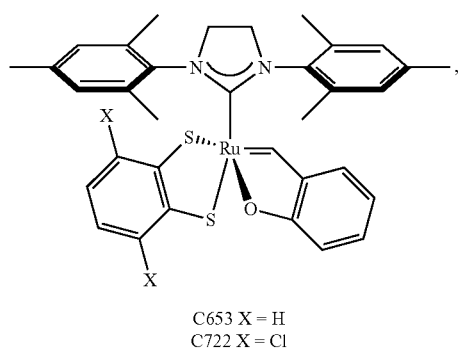
C653 X = H
C722 X = Cl
-continued
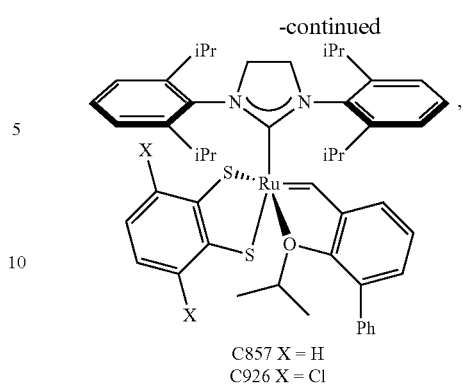
C857 X = H
C926 X = Cl
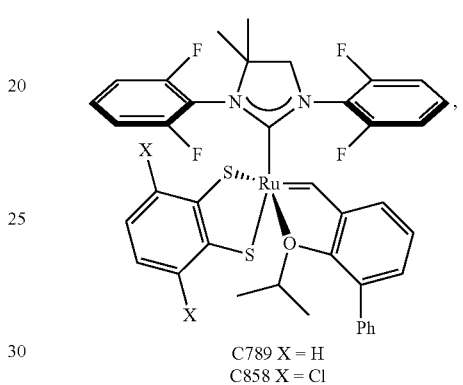
C789 X = H
C858 X = Cl
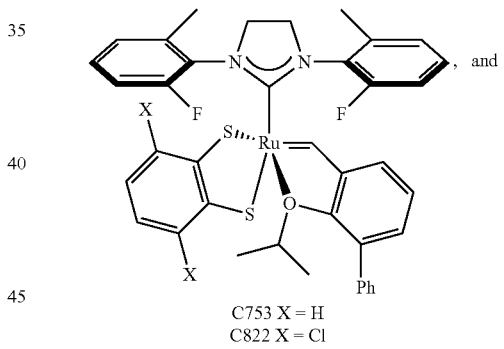
, and
C753 X = H
C822 X = Cl
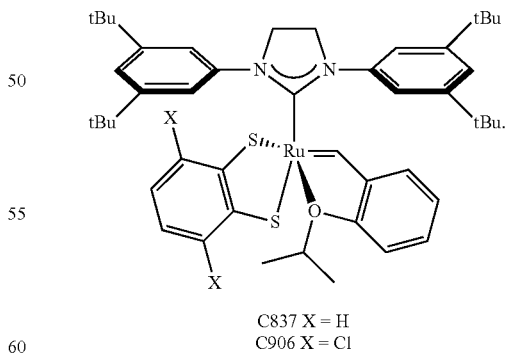
C837 X = H
C906 X = Cl
In another embodiment the invention provides a method for generating Z-macrocycles via macrocyclic ring-closing metathesis of diene substrate bearing a Z-olefin moiety in the presence of a stereoretentive Ru-based catalyst of Formula (II):

Formula (II)

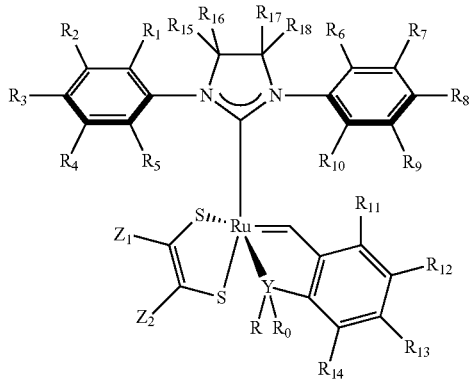

wherein:
R and $R_0$ are independently nil, H, methyl, ethyl, propyl, iso-propyl, butyl, sec-butyl, tert-butyl, or phenyl;
$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano;
$R_{15}$, $R_{16}$, $R_{17}$, and $R_{18}$ are independently H or methyl;
$Z_1$ and $Z_2$ are independently cyano or nitro; and
Y is oxygen, sulfur, nitrogen, or iodo.

In another embodiment the invention provides a method for generating Z-macrocycles via macrocyclic ring-closing metathesis of diene substrate bearing a Z-olefin moiety in the presence of a stereoretentive Ru-based catalyst of Formula (II), wherein:
R is iso-propyl;
$R_0$ is nil;
$R_1$, $R_2$, $R_3$, $R_4$, $R_5$, $R_6$, $R_7$, $R_8$, $R_9$, and $R_{10}$ are independently H or methyl;
$R_{11}$, $R_{12}$, $R_{13}$, and $R_{14}$ are independently H;
$R_{15}$, $R_{16}$, $R_{17}$, and $R_{18}$ are independently H;
$Z_1$ and $Z_2$ are independently cyano; and
Y is oxygen or sulfur.

In another embodiment the invention provides a method for generating Z-macrocycles via macrocyclic ring-closing metathesis of diene substrate bearing a Z-olefin moiety in the presence of a stereoretentive Ru-based catalyst of Formula (II), wherein:
R is iso-propyl;
$R_0$ is nil;
$R_1$ is methyl;
$R_2$ is H;
$R_3$ is methyl;
$R_4$ is H;
$R_5$ is methyl;
$R_6$ is methyl;
$R_7$ is H;
$R_8$ is methyl;
$R_9$ is H;
$R_{10}$ is methyl;
$R_{11}$, $R_{12}$, $R_{13}$, and $R_{14}$ are H;
$R_{15}$, $R_{16}$, $R_{17}$, and $R_{18}$ are H;
$Z_1$ and $Z_2$ are cyano; and
Y is oxygen or sulfur.

In another embodiment the invention provides a method for generating Z-macrocycles via macrocyclic ring-closing metathesis of diene substrate bearing a Z-olefin moiety in the presence of a stereoretentive Ru-based catalyst selected from:

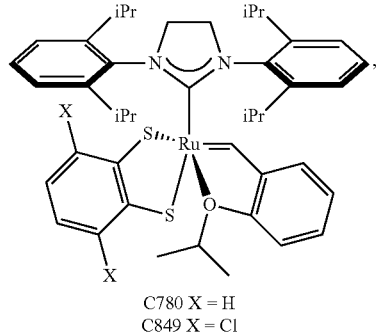

C780 X = H
C849 X = Cl

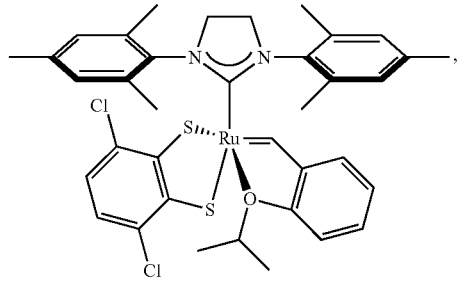

C765

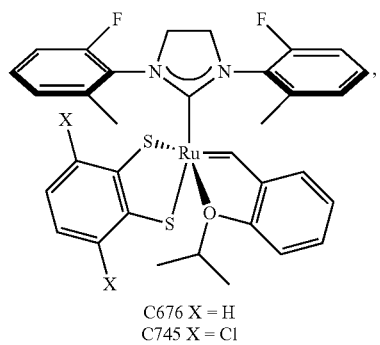

C676 X = H
C745 X = Cl

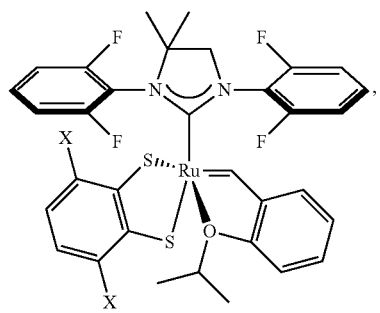

C712f X = H
C781 X = Cl

-continued
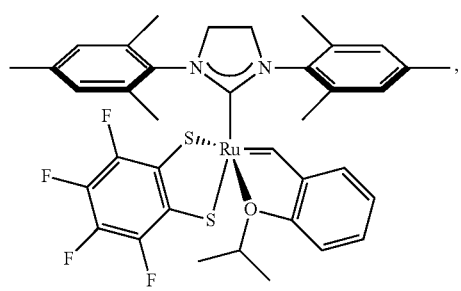
C768
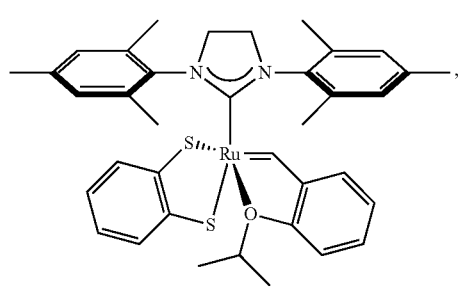
C696
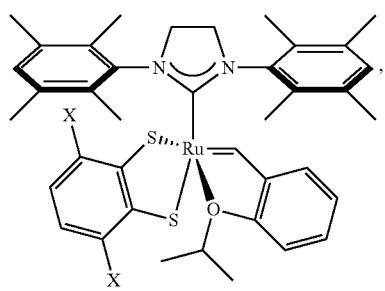
C724 X = H
C793 X = Cl
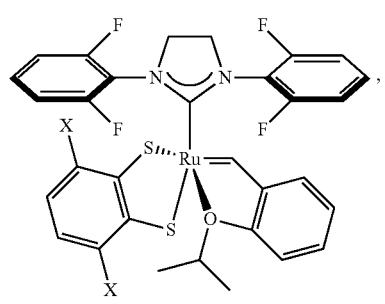
C684 X = H
C752 X = Cl
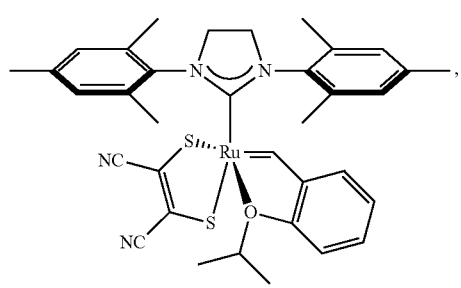
C696cn
-continued
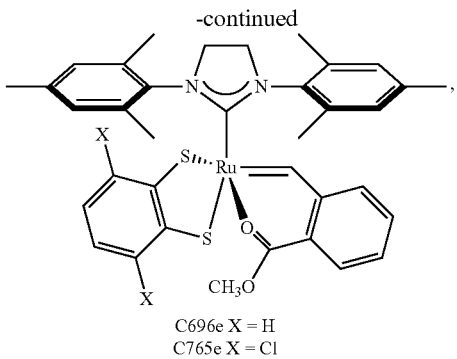
C696e X = H
C765e X = Cl
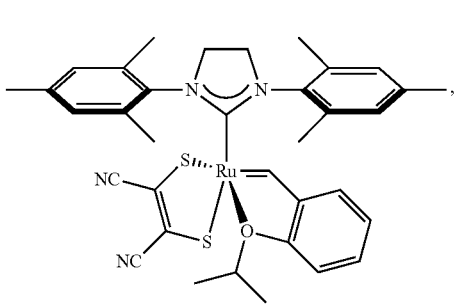
C712
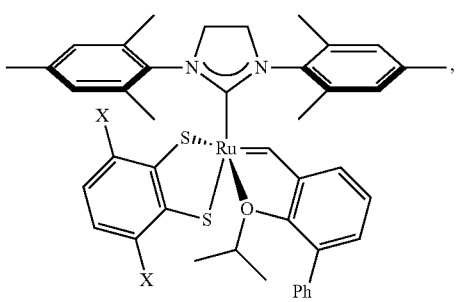
C772 X = H
C841 X = Cl
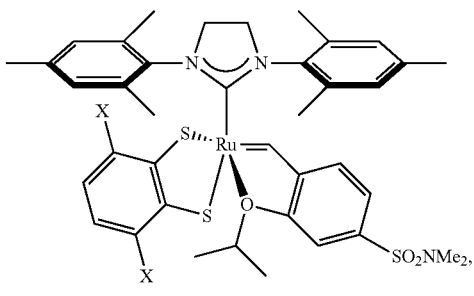
C803 X = H
C872 X = Cl
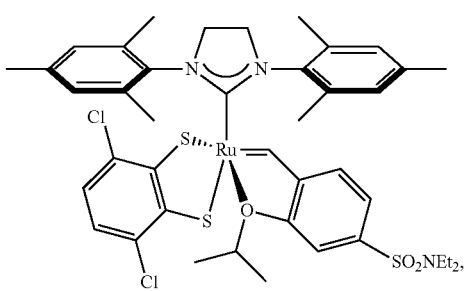
C832 X = H
C901 X = Cl -continued
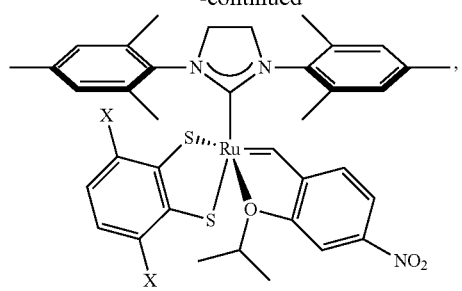
C741 X = H
C810 X = Cl
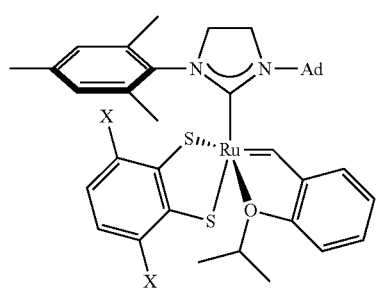
C712 X = H
C781 X = Cl
Ad = adamantyl
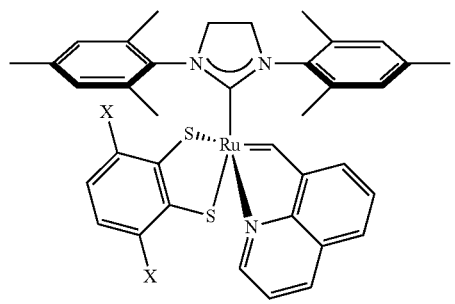
C689 X = H
C758 X = Cl
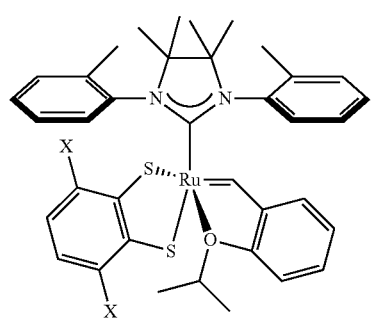
C696h X = H
C765 X = Cl
-continued
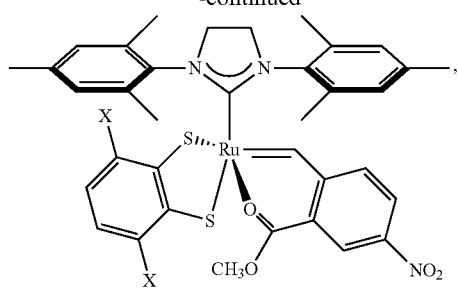
C741 X = H
C810e X = Cl
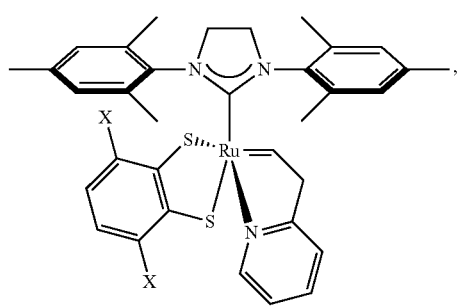
C653 X = H
C722 X = Cl
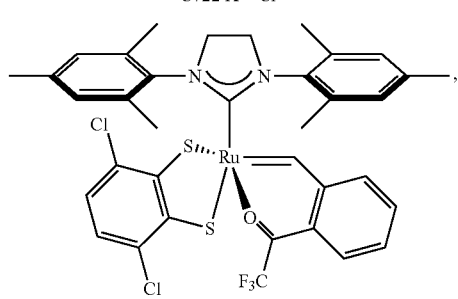
C734 X = H
C803f X = Cl
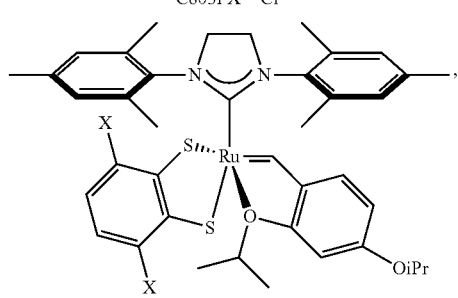
C754 X = H
C823 X = Cl
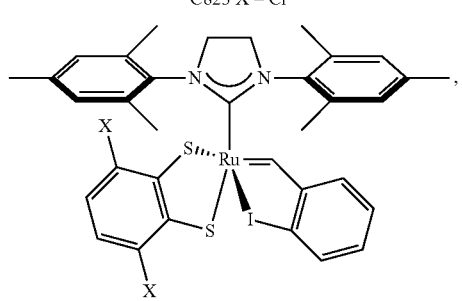
C764 X = H
C823 X = Cl -continued
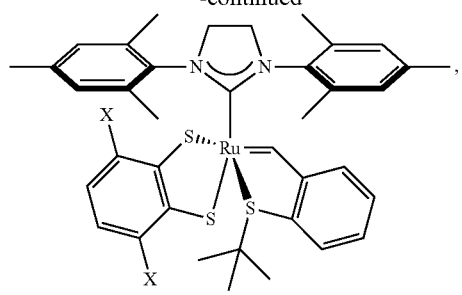
C726 X = H
C795 X = Cl
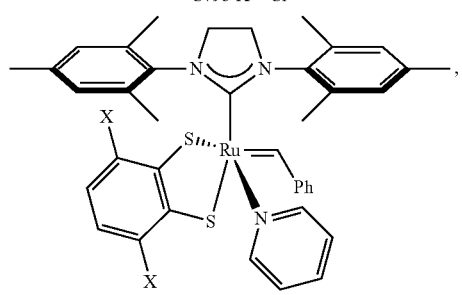
C717 X = H
C786 X = Cl
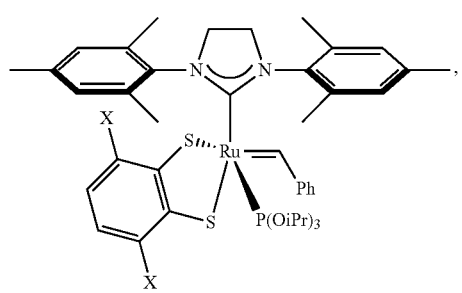
C746 X = H
C915 X = Cl
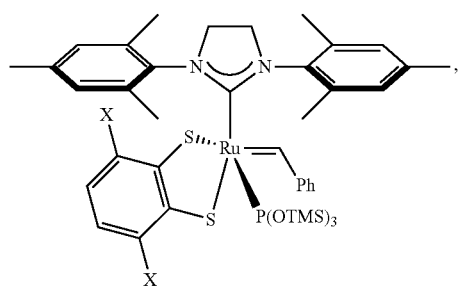
C936 X = H
C1005 X = Cl
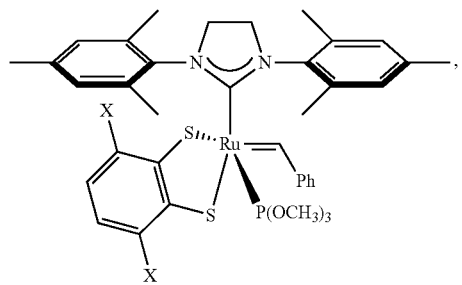
C762 X = H
C831 X = Cl
-continued
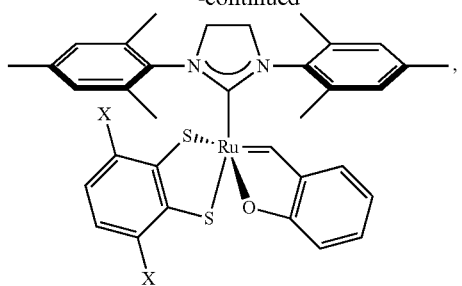
C653 X = H
C722 X = Cl
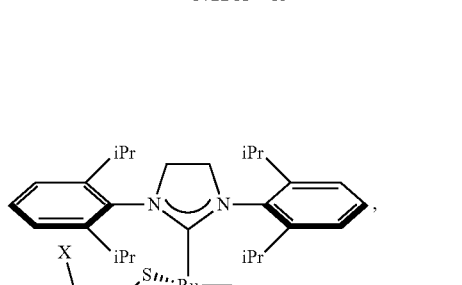
C857 X = H
C926 X = Cl
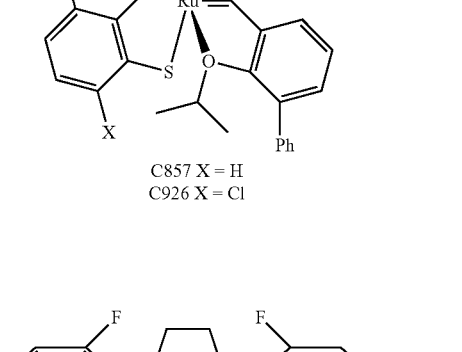
C789 X = H
C858 X = Cl
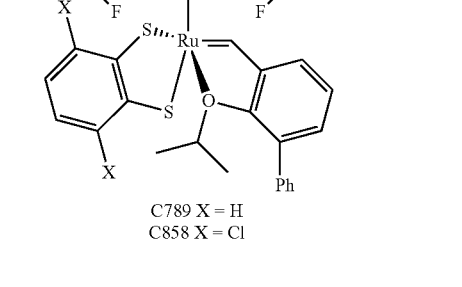
, and
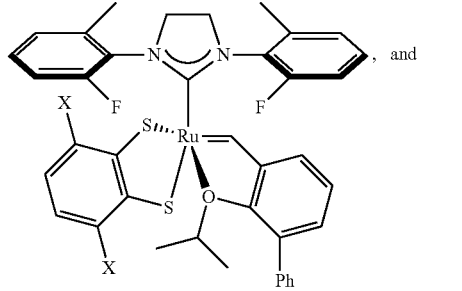
C753 X = H
C822 X = Cl -continued

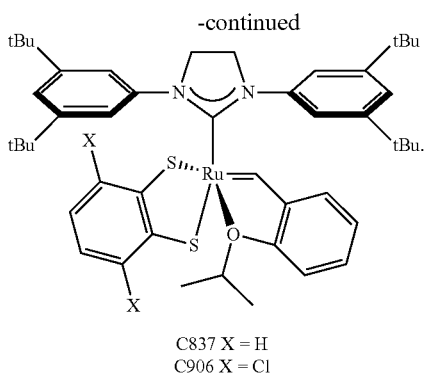

C837 X = H
C906 X = Cl

Diene Substrates Bearing a Z-Olefin Moiety

An example of a diene substrate bearing a Z-olefin moiety for use in the present invention may be represented by Formula (III):

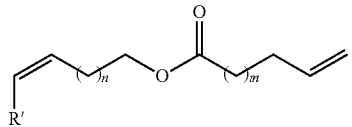

Formula (III)

wherein:
R' is methyl, ethyl, or propyl; n is 1, 2, 3, or 4; and m is 4, 5, 6, or 7.

In one embodiment, the diene substrate bearing a Z-olefin moiety is represented by Formula (III), wherein R' is methyl or ethyl; n is 1, 2, 3, or 4; and m is 4, 6, or 7.

In one embodiment, the diene substrate bearing a Z-olefin moiety is represented by Formula (III), wherein R' is methyl; n is 2; and m is 4 or 6.

In one embodiment, the diene substrate bearing a Z-olefin moiety is represented by Formula (III), wherein R' is methyl; n is 3; and m is 7.

In one embodiment, the diene substrate bearing a Z-olefin moiety can be represented by Formula (III), wherein R' is ethyl; n is 1, 2, 3, or 4; and m is 6 or 7.

In one embodiment, the diene substrate bearing a Z-olefin moiety can be represented by Formula (III), wherein R' is ethyl; n is 1 or 2; and m is 6.

In one embodiment, the diene substrate bearing a Z-olefin moiety can be represented by Formula (III), wherein R' is ethyl; n is 1, 2, 3, or 4; and m is 7.

In one embodiment, the diene substrate bearing a Z-olefin moiety can be represented by Formula (III), wherein R' is ethyl; n is 1; and m is 6.

In one embodiment, the diene substrate bearing a Z-olefin moiety can be represented by Formula (IV):

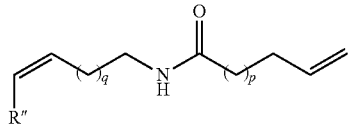

Formula (IV)

wherein:
R" is methyl, ethyl, or propyl; q is 1, 2, 3, or 4; and p is 4, 5, 6, or 7.

In one embodiment, the diene substrate bearing a Z-olefin moiety is represented by Formula (IV), wherein R" is methyl or ethyl; q is 1, 2, 3, or 4; and p is 4, 6, or 7.

In one embodiment, the diene substrate bearing a Z-olefin moiety can be represented by Formula (IV), wherein R" is methyl; q is 2; and p is 4 or 6.

In one embodiment, the diene substrate bearing a Z-olefin moiety can be represented by Formula (IV), wherein R" is ethyl; q is 1, 2, 3, or 4; and p is 6 or 7.

In one embodiment, the diene substrate bearing a Z-olefin moiety can be represented by Formula (IV), wherein R" is ethyl; q is 1 or 2; and p is 6.

In one embodiment, the diene substrate bearing a Z-olefin moiety can be represented by Formula (IV), wherein R" is ethyl; q is 1, 2, 3, or 4; and p is 7.

In one embodiment, the diene substrate bearing a Z-olefin moiety can be represented by Formula (IV), wherein R" is ethyl; q is 1; and p is 6.

Another example of a diene substrate bearing a Z-olefin moiety for use in the present invention may be represented by Formula (V):

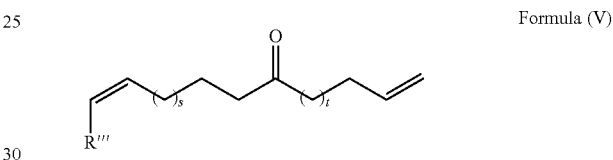

Formula (V)

wherein:
R'" is methyl, ethyl, or propyl; s is 1, 2, 3, or 4; and t is 4, 5, 6, or 7.

In one embodiment, the diene substrate bearing a Z-olefin moiety is represented by Formula (V), wherein R'" is methyl or ethyl; s is 1, 2, 3, or 4; and t is 4, 6, or 7.

In one embodiment, the diene substrate bearing a Z-olefin moiety is represented by Formula (V), wherein R'" is methyl; s is 2; and t is 4 or 6.

In one embodiment, the diene substrate bearing a Z-olefin moiety can be represented by Formula (V), wherein R'" is ethyl; s is 1, 2, 3, or 4; and t is 6 or 7.

In one embodiment, the diene substrate bearing a Z-olefin moiety can be represented by Formula (V), wherein R'" is ethyl; s is 1 or 2; and t is 6.

In one embodiment, the diene substrate bearing a Z-olefin moiety can be represented by Formula (V), wherein R'" is ethyl; s is 1, 2, 3, or 4; and t is 7.

In one embodiment, the diene substrate bearing a Z-olefin moiety can be represented by Formula (V), wherein R'" is ethyl; s is 1; and t is 6.

Z-Macrocyclic Products

The Z-macrocyclic product of the invention, comprises an internal olefin, wherein the internal olefin is in a Z-selectivity of 90%, or of 95%, or of 99%.

In some embodiments, the invention provides a method that produces a compound (i.e., a product, olefin product; e.g., ring-close metathesis product, a Z-macrocyclic product) having a carbon-carbon double bond (e.g., a product internal olefin) in a Z/E selectivity ratio of 95/5, or 96/4, or 97/3, or 98/2, or in some cases, of 99/1. In some cases, 100% of the carbon-carbon double bond produced in the metathesis reaction may have a Z-configuration. The Z- or cis selectivity may also be expressed as a percentage of product formed (e.g., ring-close metathesis product, Z-macrocyclic product).

In one embodiment, the Z-macrocyclic product has a carbon-carbon double bond in a Z-configuration and is represented by the structure of Formula (VI):

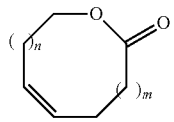

Formula (VI)

wherein:
n is 1, 2, 3, or 4; and m is 4, 5, 6, or 7.

In another embodiment, the at least one Z-macrocyclic product is represented by the structure of Formula (VI), wherein n is 1, 2, 3, or 4; and m is 4, 6, or 7.

In another embodiment, the at least one Z-macrocyclic product is represented by the structure of Formula (VI), wherein n is 2; and m is 4 or 6.

In another embodiment, the at least one Z-macrocyclic product is represented by the structure of Formula (VI), wherein n is 3; and m is 7.

In another embodiment, the at least one Z-macrocyclic product is represented by the structure of Formula (VI), wherein n is 1, 2, 3, or 4; and m is 6 or 7.

In another embodiment, the at least one Z-macrocyclic product is represented by the structure of Formula (VI), wherein, n is 1 or 2; and m is 6.

In another embodiment, the at least one Z-macrocyclic product is represented by the structure of Formula (VI), wherein n is 1, 2, 3, or 4; and m is 7.

In another embodiment, the at least one Z-macrocyclic product is represented by the structure of Formula (VI), wherein, n is 1; and m is 6.

In one embodiment, the at least one Z-macrocyclic product has a carbon-carbon double bond in a Z-configuration and is represented by the structure of Formula (VII):

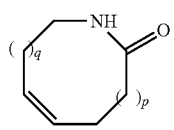

Formula (VII)

wherein:
q is 1, 2, 3, or 4; and p is 4, 5, 6, or 7.

In another embodiment, the at least one Z-macrocyclic product is represented by the structure of Formula (VII), wherein q is 1, 2, 3, or 4; and p is 4, 6, or 7.

In another embodiment, the at least one Z-macrocyclic product is represented by the structure of Formula (VII), wherein q is 2; and p is 4 or 6.

In another embodiment, the at least one Z-macrocyclic product is represented by the structure of Formula (VII), wherein q is 1, 2, 3, or 4; and p is 6 or 7.

In another embodiment, the at least one Z-macrocyclic product is represented by the structure of Formula (VII), wherein, q is 1 or 2; and p is 6.

In another embodiment, the at least one Z-macrocyclic product is represented by the structure of Formula (VII), wherein q is 1, 2, 3, or 4; and p is 7.

In another embodiment, the at least one Z-macrocyclic product is represented by the structure of Formula (VII), wherein q is 1; and p is 6.

In o embodiment, the Z-macrocyclic product has a carbon-carbon double bond in a Z-configuration and is represented by the structure of Formula (VIII):

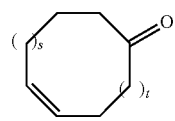

Formula (VIII)

wherein:
s is 1, 2, 3, or 4; and t is 4, 5, 6, or 7.

In another embodiment, the at least one Z-macrocyclic product is represented by the structure of Formula (VIII), wherein s is 1, 2, 3, or 4; and t is 4, 6, or 7.

In another embodiment, the at least one Z-macrocyclic product is represented by the structure of Formula (VIII), wherein s is 2; and t is 4 or 6.

In another embodiment, the at least one Z-macrocyclic product is represented by the structure of Formula (VIII), wherein s is 1, 2, 3, or 4; and t is 6 or 7.

In another embodiment, the at least one Z-macrocyclic product is represented by the structure of Formula (VIII), wherein, s is 1 or 2; and t is 6.

In another embodiment, the at least one Z-macrocyclic product is represented by the structure of Formula (VIII), wherein s is 1, 2, 3, or 4; and t is 7.

In another embodiment, the at least one Z-macrocyclic product is represented by the structure of Formula (VIII), wherein, s is 1; and t is 6.

EMBODIMENTS

In one embodiment, the invention provides a method for producing at least one Z-macrocyclic product represented by Formula (VI):

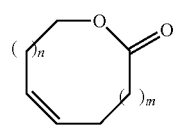

Formula (VI)

wherein:
n is 1, 2, 3, or 4; m is 4, 5, 6, or 7; and the Z-macrocyclic product of Formula (VI) is a twelve, thirteen, fourteen, fifteen, sixteen, or seventeen-membered ring with a Z-selectivity of 95, or 98, or 99; comprising:
subjecting a diene substrate bearing a Z-olefin moiety represented by Formula (III):

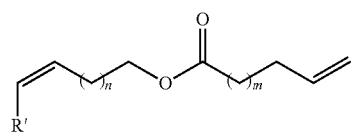

Formula (III)

wherein:
R' is methyl, ethyl, or propyl; n is 1, 2, 3, or 4; m is 4, 5, 6, or 7;
to a macrocyclic ring-closing metathesis reaction in the presence of a stereoretentive Ru-based catalyst represented by Formula (I):

Formula (I)

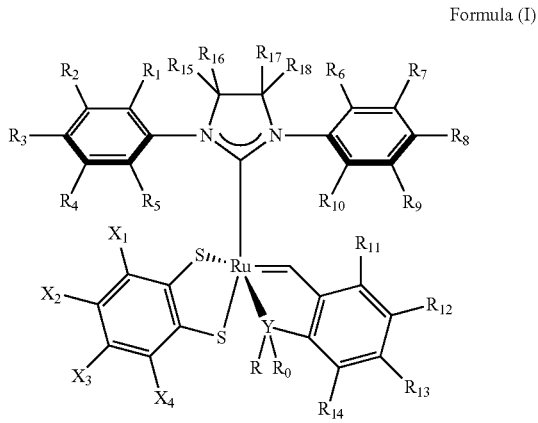

Formula (II)

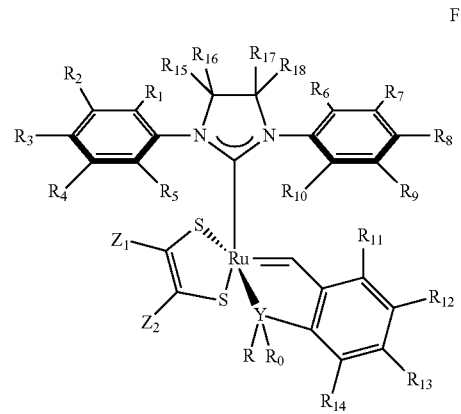

wherein:

R and $R_0$ are independently nil, H, methyl, ethyl, propyl, iso-propyl, butyl, sec-butyl, tert-butyl, or phenyl;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, iso-propoxy, butyl, sec-butyl, tert-butyl, phenyl, fluoro, chloro, bromo, iodo, nitro, dimethylaminosulfonate, diethylaminosulfonate, or cyano;

$R_{15}$, $R_{16}$, $R_{17}$, and $R_{18}$ are independently H or methyl;

$X_1$, $X_2$, $X_3$, and $X_4$ are independently H, fluoro, chloro, bromo, iodo, methyl, ethyl, propyl, iso-propyl, butyl, sec-butyl, tert-butyl, or phenyl; and Y is oxygen, sulfur, nitrogen, or iodo.

In one embodiment, the invention provides a method for producing at least one Z-macrocyclic product represented by Formula (VI):

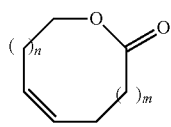

Formula (VI)

wherein:

n is 1, 2, 3, or 4; m is 4, 5, 6, or 7; and the Z-macrocyclic product of Formula (VI) is a twelve, thirteen, fourteen, fifteen, sixteen, or seventeen-membered ring with a Z-selectivity of 95, or 98, or 99; comprising:

subjecting a diene substrate bearing a Z-olefin moiety represented by Formula (III):

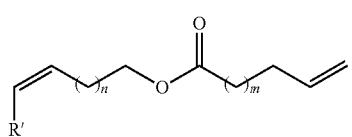

Formula (III)

wherein:

R' is methyl, ethyl, or propyl; n is 1, 2, 3, or 4; m is 4, 5, 6, or 7;

to a macrocyclic ring-closing metathesis reaction in the presence of a stereoretentive Ru-based catalyst represented by Formula (II):

wherein:

R and $R_0$ are independently nil, H, methyl, ethyl, propyl, iso-propyl, butyl, sec-butyl, tert-butyl, or phenyl;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano;

$R_{15}$, $R_{16}$, $R_{17}$, and $R_{18}$ are independently H or methyl;

$Z_1$ and $Z_2$ are independently cyano or nitro; and

Y is oxygen, sulfur, nitrogen, or iodo.

In one embodiment, the invention provides a method for producing at least one Z-macrocyclic product represented by Formula (VII):

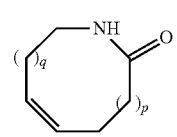

Formula (VII)

wherein:

q is 1, 2, 3, or 4; p is 4, 5, 6, or 7; and the Z-macrocyclic product of Formula (VII) is a twelve, thirteen, fourteen, fifteen, sixteen, or seventeen-membered ring with a Z-selectivity of 95, or 98, or 99; comprising:

subjecting a diene substrate bearing a Z-olefin moiety represented by Formula (IV):

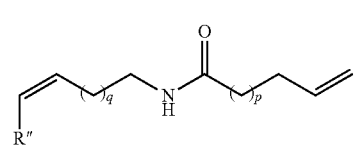

Formula (IV)

wherein:

R" is methyl, ethyl, or propyl; q is 1, 2, 3, or 4; p is 4, 5, 6, or 7;

to a macrocyclic ring-closing metathesis reaction in the presence of a stereoretentive Ru-based catalyst represented by Formula (I):

Formula (I)

[Structure of Formula (I) showing Ru-based catalyst with substituents $R_1$-$R_{18}$, $X_1$-$X_4$, $R$, $R_0$, and Y]

wherein:

R and $R_0$ are independently nil, H, methyl, ethyl, propyl, iso-propyl, butyl, sec-butyl, tert-butyl, or phenyl;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, iso-propoxy, butyl, sec-butyl, tert-butyl, phenyl, fluoro, chloro, bromo, iodo, nitro, dimethylaminosulfonate, diethylaminosulfonate, or cyano;

$R_{15}$, $R_{16}$, $R_{17}$, and $R_{18}$ are independently H or methyl;

$X_1$, $X_2$, $X_3$, and $X_4$ are independently H, fluoro, chloro, bromo, iodo, methyl, ethyl, propyl, iso-propyl, butyl, sec-butyl, tert-butyl, or phenyl; and Y is oxygen, sulfur, nitrogen, or iodo.

In one embodiment, the invention provides a method for producing at least one Z-macrocyclic product represented by Formula (VII):

Formula (VII)

[Structure showing a macrocyclic ring with NH, C=O, and (q, p) repeating units with a Z-olefin]

wherein:

q is 1, 2, 3, or 4; p is 4, 5, 6, or 7; and the Z-macrocyclic product of Formula (VII) is a twelve, thirteen, fourteen, fifteen, sixteen, or seventeen-membered ring with a Z-selectivity of 95, or 98, or 99; comprising:

subjecting a diene substrate bearing a Z-olefin moiety represented by Formula (IV):

Formula (IV)

[Structure showing diene substrate with amide linkage and substituent R"]

wherein:

R" is methyl, ethyl, or propyl; q is 1, 2, 3, or 4; p is 4, 5, 6, or 7;

to a macrocyclic ring-closing metathesis reaction in the presence of a stereoretentive Ru-based catalyst represented by Formula (II):

Formula (II)

[Structure of Formula (II) showing Ru-based catalyst with substituents $R_1$-$R_{18}$, $Z_1$, $Z_2$, $R$, $R_0$, and Y]

wherein:

R and $R_0$ are independently nil, H, methyl, ethyl, propyl, iso-propyl, butyl, sec-butyl, tert-butyl, or phenyl;

$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano;

$R_{15}$, $R_{16}$, $R_{17}$, and $R_{18}$ are independently H or methyl;

$Z_1$ and $Z_2$ are independently cyano or nitro; and

Y is oxygen, sulfur, nitrogen, or iodo.

In one embodiment, the invention provides a method for producing at least one Z-macrocyclic product represented by Formula (VI), wherein: n is 1, 2, 3, or 4; m is 4, 5, 6, or 7; and the Z-macrocyclic product of Formula (VI) is an eleven, twelve, thirteen, fourteen, fifteen, sixteen, or seventeen-membered ring with a Z-selectivity of 95, or 98, or 99; comprising: subjecting a diene substrate bearing a Z-olefin moiety represented by Formula (III), wherein: R' is methyl, ethyl, or propyl; n is 1, 2, 3, or 4; m is 4, 5, 6, or 7; to a macrocyclic ring-closing metathesis reaction in the presence of a stereoretentive Ru-based catalyst represented by Formula (I), wherein: R and $R_0$ are independently nil, H, methyl, ethyl, propyl, iso-propyl, butyl, sec-butyl, tert-butyl, or phenyl; $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, iso-propoxy, butyl, sec-butyl, tert-butyl, phenyl, fluoro, chloro, bromo, iodo, nitro, dimethylaminosulfonate, diethylaminosulfonate, or cyano; $R_{15}$, $R_{16}$, $R_{17}$, and $R_{18}$ are independently H or methyl; $X_1$, $X_2$, $X_3$, and $X_4$ are independently H, fluoro, chloro, bromo, iodo, methyl, ethyl, propyl, iso-propyl, butyl, sec-butyl, tert-butyl, or phenyl; and Y is oxygen, sulfur, nitrogen, or iodo.

In one embodiment, the invention provides a method for producing at least one Z-macrocyclic product represented by Formula (VI), wherein: n is 1, 2, 3, or 4; m is 4, 5, 6, or 7; and the Z-macrocyclic product of Formula (VI) is an eleven, twelve, thirteen, fourteen, fifteen, sixteen, or seventeen-membered ring with a Z-selectivity of 95, or 98, or 99; comprising: subjecting a diene substrate bearing a Z-olefin moiety represented by Formula (III) wherein: R' is methyl, ethyl, or propyl; n is 1, 2, 3, or 4; m is 4, 5, 6, or 7; to a macrocyclic ring-closing metathesis reaction in the presence of a stereoretentive Ru-based catalyst represented by Formula (II), wherein, R and $R_0$ are independently nil, H, methyl, ethyl, propyl, iso-propyl, butyl, sec-butyl, tert-butyl, or phenyl; $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano; $R_{15}$, $R_{16}$, $R_{17}$, and $R_{18}$ are independently H or methyl; $Z_1$ and $Z_2$ are independently cyano or nitro; and Y is oxygen, sulfur, nitrogen, or iodo.

In one embodiment, the invention provides a method for producing at least one Z-macrocyclic product represented by Formula (VII), wherein: q is 1, 2, 3, or 4; p is 4, 5, 6, or 7; and the Z-macrocyclic product of Formula (VII) is an eleven, twelve, thirteen, fourteen, fifteen, sixteen, or seventeen-membered ring with a Z-selectivity of 95, or 98, or 99; comprising: subjecting a diene substrate bearing a Z-olefin moiety represented by Formula (IV) wherein: R" is methyl, ethyl, or propyl; q is 1, 2, 3, or 4; p is 4, 5, 6, or 7; to a macrocyclic ring-closing metathesis reaction in the presence of a stereoretentive Ru-based catalyst represented by Formula (I), wherein: R and $R_0$ are independently nil, H, methyl, ethyl, propyl, iso-propyl, butyl, sec-butyl, tert-butyl, or phenyl; $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, iso-propoxy, butyl, sec-butyl, tert-butyl, phenyl, fluoro, chloro, bromo, iodo, nitro, dimethylaminosulfonate, diethylaminosulfonate, or cyano; $R_{15}$, $R_{16}$, $R_{17}$, and $R_{18}$ are independently H or methyl; $X_1$, $X_2$, $X_3$, and $X_4$ are independently H, fluoro, chloro, bromo, iodo, methyl, ethyl, propyl, iso-propyl, butyl, sec-butyl, tert-butyl, or phenyl; and Y is oxygen, sulfur, nitrogen, or iodo.

In one embodiment, the invention provides a method for producing at least one Z-macrocyclic product represented by Formula (VII), wherein: q is 1, 2, 3, or 4; p is 4, 5, 6, or 7; and the Z-macrocyclic product of Formula (VII) is an eleven, twelve, thirteen, fourteen, fifteen, sixteen, or seventeen-membered ring with a Z-selectivity of 95, or 98, or 99; comprising: subjecting a diene substrate bearing a Z-olefin moiety represented by Formula (IV) wherein: R" is methyl, ethyl, or propyl; q is 1, 2, 3, or 4; p is 4, 5, 6, or 7; to a macrocyclic ring-closing metathesis reaction in the presence of a stereoretentive Ru-based catalyst represented by Formula (II), wherein, R and $R_0$ are independently nil, H, methyl, ethyl, propyl, iso-propyl, butyl, sec-butyl, tert-butyl, or phenyl; $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano; $R_{15}$, $R_{16}$, $R_{17}$, and $R_{18}$ are independently H or methyl; $Z_1$ and $Z_2$ are independently cyano or nitro; and Y is oxygen, sulfur, nitrogen, or iodo.

In one embodiment, the invention provides a method for producing at least one Z-macrocyclic product represented by Formula (VII):

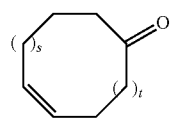

Formula (VIII)

wherein:
s is 1, 2, 3, or 4; t is 4, 5, 6, or 7; and the Z-macrocyclic product of Formula (VIII) is an eleven, twelve, thirteen, fourteen, fifteen, sixteen, or seventeen-membered ring with a Z-selectivity of 95, or 98, or 99; comprising:

subjecting a diene substrate bearing a Z-olefin moiety represented by Formula (V):

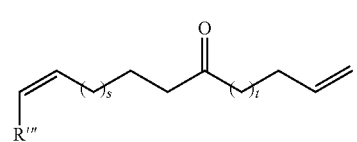

Formula (V)

wherein:
R''' is methyl, ethyl, or propyl; s is 1, 2, 3, or 4; t is 4, 5, 6, or 7;
to a macrocyclic ring-closing metathesis reaction in the presence of a stereoretentive Ru-based catalyst represented by Formula (I):

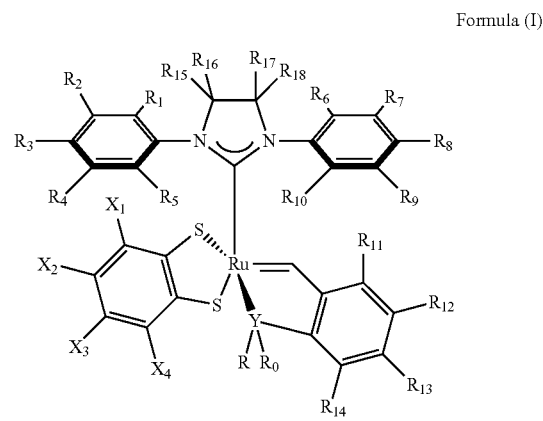

Formula (I)

wherein:
R and $R_0$ are independently nil, H, methyl, ethyl, propyl, iso-propyl, butyl, sec-butyl, tert-butyl, or phenyl;
$R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently H, methyl, ethyl, propyl, iso-propyl, iso-propoxy, butyl, sec-butyl, tert-butyl, phenyl, fluoro, chloro, bromo, iodo, nitro, dimethylaminosulfonate, diethylaminosulfonate, or cyano;
$R_{15}$, $R_{16}$, $R_{17}$, and $R_{18}$ are independently H or methyl;
$X_1$, $X_2$, $X_3$, and $X_4$ are independently H, fluoro, chloro, bromo, iodo, methyl, ethyl, propyl, iso-propyl, butyl, sec-butyl, tert-butyl, or phenyl; and
Y is oxygen, sulfur, nitrogen, or iodo.

In one embodiment, the invention provides a method for producing at least one Z-macrocyclic product represented by Formula (VIII):

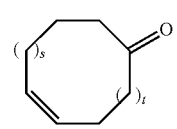

Formula (VIII)

wherein:
s is 1, 2, 3, or 4; t is 4, 5, 6, or 7; and the Z-macrocyclic product of Formula (VIII) is an eleven, twelve, thirteen, fourteen, fifteen, sixteen, or seventeen-membered ring with a Z-selectivity of 95, or 98, or 99; comprising:

subjecting a diene substrate bearing a Z-olefin moiety represented by Formula (V):

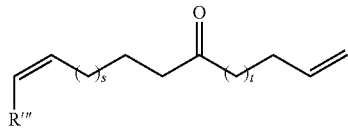

Formula (V)

wherein:
R''' is methyl, ethyl, or propyl; s is 1, 2, 3, or 4; t is 4, 5, 6, or 7;
to a macrocyclic ring-closing metathesis reaction in the presence of a stereoretentive Ru-based catalyst represented by Formula (II):

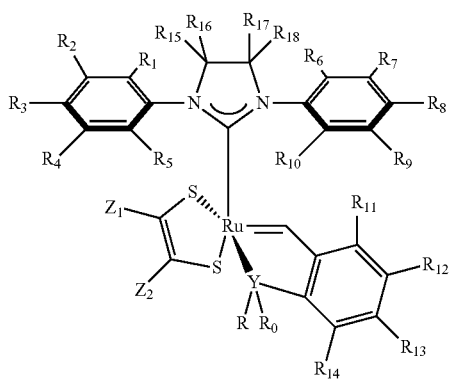

Formula (II)

wherein:
R and $R_0$ are independently nil, H, methyl, ethyl, propyl, iso-propyl, butyl, sec-butyl, tert-butyl, or phenyl;
$R_1, R_2, R_3, R_4, R_5, R_6, R_7, R_8, R_9, R_{10}, R_{11}, R_{12}, R_{13}$, and $R_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano;
$R_{15}, R_{16}, R_{17}$, and $R_{18}$ are independently H or methyl;
$Z_1$ and $Z_2$ are independently cyano or nitro; and
Y is oxygen, sulfur, nitrogen, or iodo.

In one embodiment, the invention provides a method for producing at least one Z-macrocyclic product as described above, comprising: subjecting a diene substrate bearing a Z-olefin moiety as described above, to a macrocyclic ring-closing metathesis reaction in the presence of a stereoretentive Ru-based catalyst selected from:

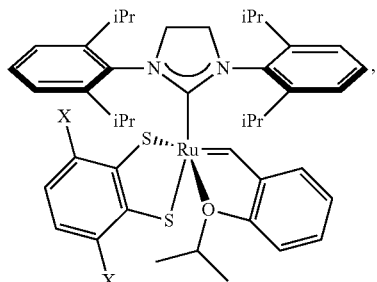

C780 X = H
C849 X = Cl

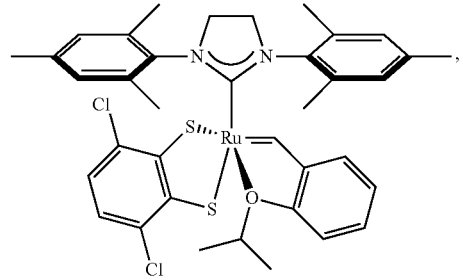

C765

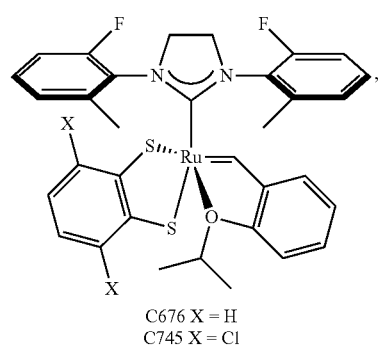

C676 X = H
C745 X = Cl

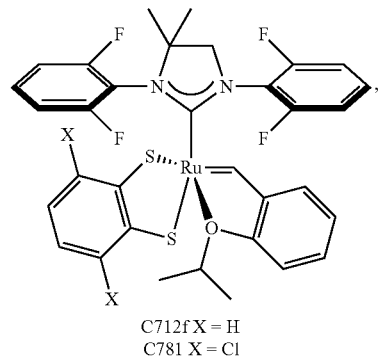

C712f X = H
C781 X = Cl

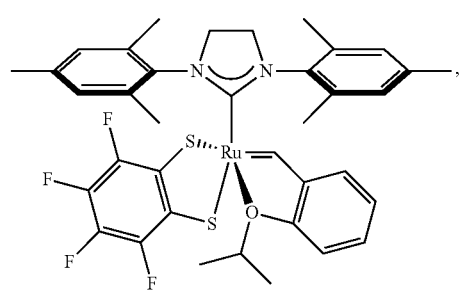

C768

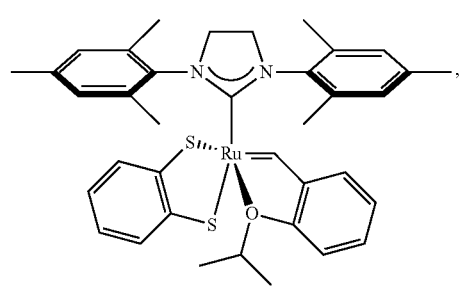

C696

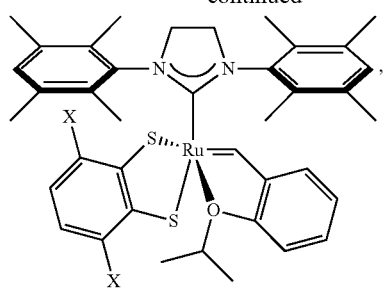
C724 X = H
C793 X = Cl
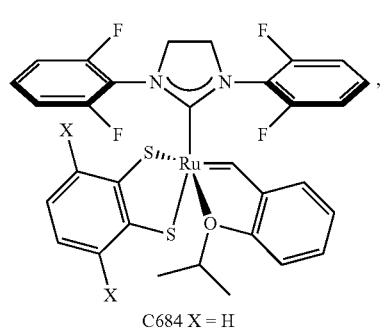
C684 X = H
C752 X = Cl
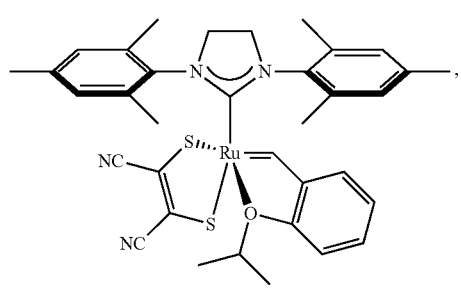
C696cn
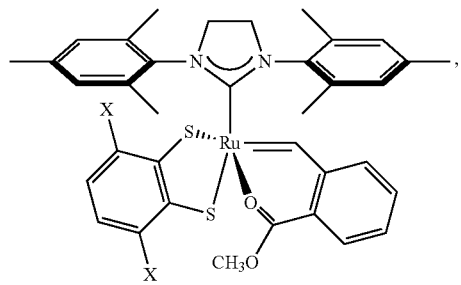
C696e X = H
C765e X = Cl
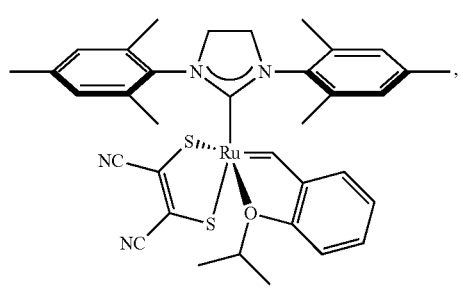
C712
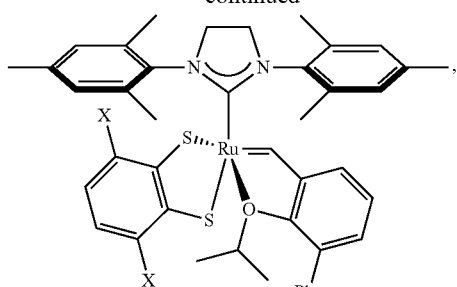
C772 X = H
C841 X = Cl
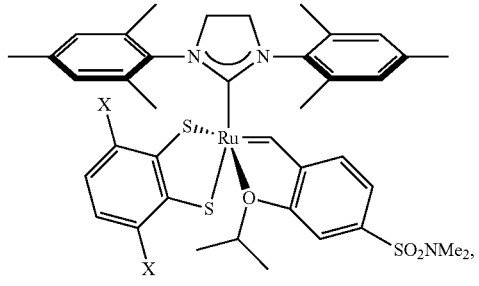
C803 X = H
C872 X = Cl
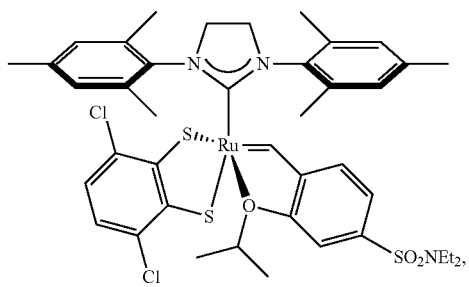
C832 X = H
C901 X = Cl
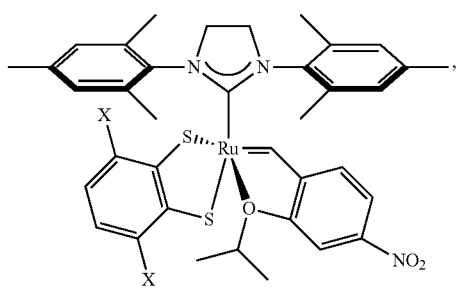
C741 X = H
C810 X = Cl
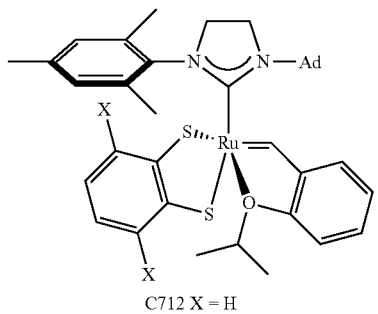
C712 X = H
C781 X = Cl
Ad = adamantyl -continued
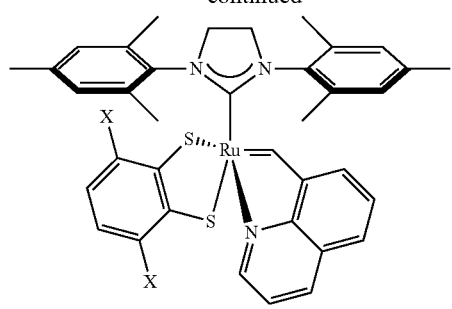
C689 X = H
C758 X = Cl
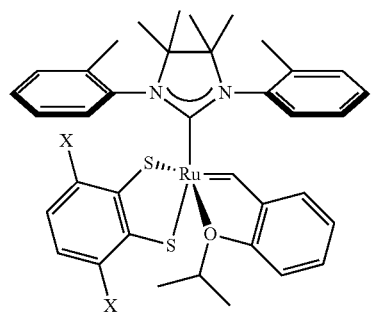
C696h X = H
C765 X = Cl
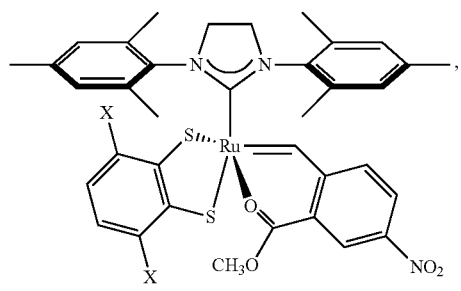
C741 X = H
C810e X = Cl
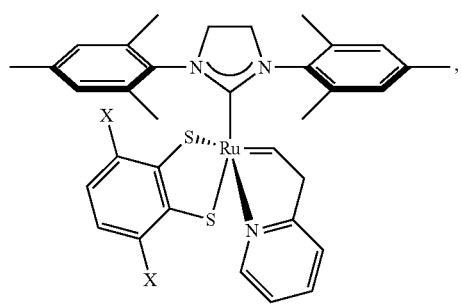
C653 X = H
C722 X = Cl
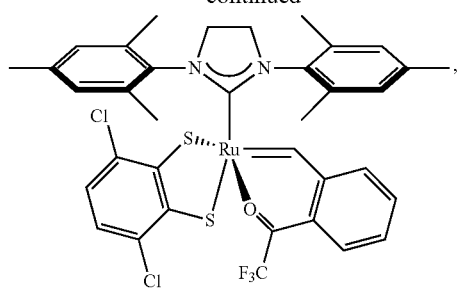
C734 X = H
C803f X = Cl
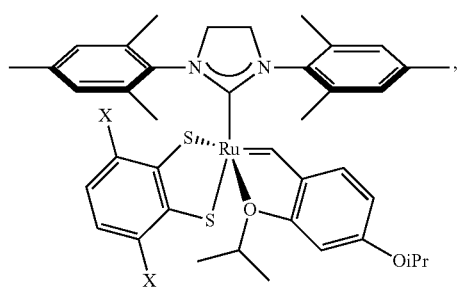
C754 X = H
C823 X = Cl
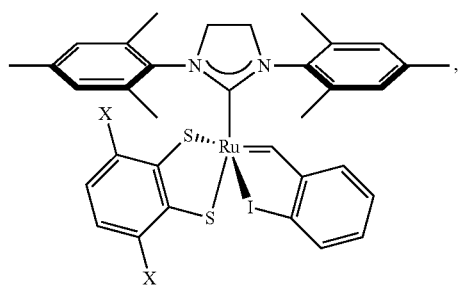
C764 X = H
C823 X = Cl
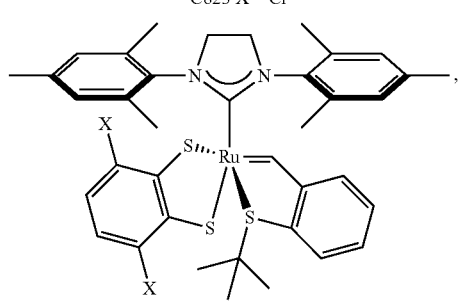
C726 X = H
C795 X = Cl
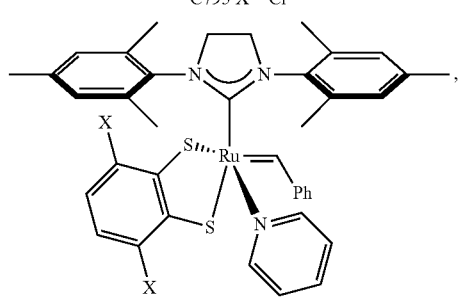
C717 X = H
C786 X = Cl

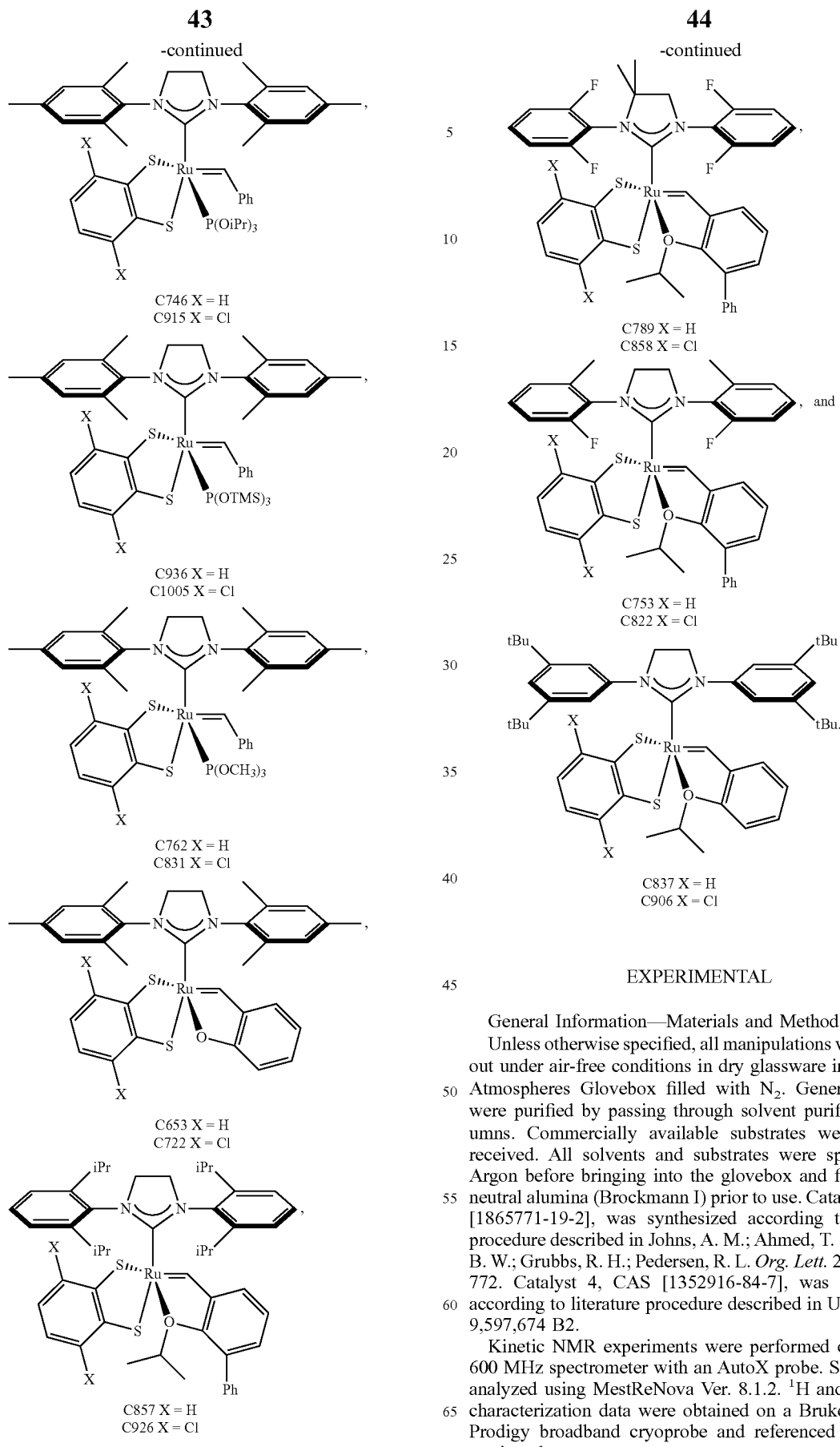

EXPERIMENTAL

General Information—Materials and Methods

Unless otherwise specified, all manipulations were carried out under air-free conditions in dry glassware in a Vacuum Atmospheres Glovebox filled with $N_2$. General solvents were purified by passing through solvent purification columns. Commercially available substrates were used as received. All solvents and substrates were sparged with Argon before bringing into the glovebox and filtered over neutral alumina (Brockmann I) prior to use. Catalyst 5, CAS [1865771-19-2], was synthesized according to literature procedure described in Johns, A. M.; Ahmed, T. S.; Jackson, B. W.; Grubbs, R. H.; Pedersen, R. L. Org. Lett. 2016, 18 (4), 772. Catalyst 4, CAS [1352916-84-7], was synthesized according to literature procedure described in U.S. Pat. No. 9,597,674 B2.

Kinetic NMR experiments were performed on a Varian 600 MHz spectrometer with an AutoX probe. Spectra were analyzed using MestReNova Ver. 8.1.2. $^1$H and $^{13}$C NMR characterization data were obtained on a Bruker 400 with Prodigy broadband cryoprobe and referenced to residual protio-solvent.

The following abbreviations are used in the examples:

| | |
|---|---|
| mL | milliliter |
| L | liter |
| ° C. | degrees Celsius |
| $CD_2Cl_2$ | deuterated dichloromethane |
| $CDCl_3$ | deuterated chloroform |
| DCM | dichloromethane |
| HCl | hydrochloric acid |
| $NaHCO_3$ | sodium dicarboxylate |
| $Et_2O$ | diethyl ether |
| $MgSO_4$ | magnesium sulfate |

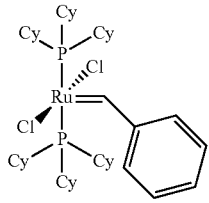

| | |
|---|---|
| C823 | Dichloro(benzylidene)bis(tricyclohexyl phosphine) ruthenium (II) [CAS 172222-30-9] |
| aq. | aqueous |
| sat. | saturated |

EXAMPLES

Synthesis of Diene Substrates Bearing a Z-olefin Moiety

Example 1

Synthesis of (Z)-hex-4-en-1-yl oct-7-enoate (6)

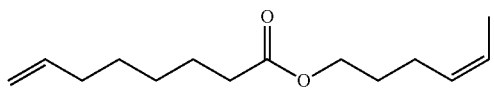 [SMILES: C=CCCCCCC(=O)OCCC/C=C\C]

To a 100 mL round-bottom flask charged with a stir bar were added dichloromethane (50 mL), 7-octenoic acid (1.54 mL, 10.0 mmol), and pyridine (80.7 μL, 1.00 mmol). Oxalyl chloride (1.00 mL, 11.8 mmol) was added dropwise, and the reaction was stirred overnight. The solvents were removed under vacuum. Dichloromethane (20 mL) and pyridine (0.81 mL, 10.0 mmol) were added, subsequently, cis-4-hexenol (1.09 mL, 9.3 mmol) was added dropwise at 0° C. After bringing the reaction to room temperature, it was stirred for an additional 4 h. The reaction mixture was extracted with 1M aq. HCl (200 mL) and sat. aq. $NaHCO_3$ (200 mL). The organic layer was dried over anhydrous $MgSO_4$, filtered, and the solvents were removed under vacuum. The product was purified by column chromatography on silica gel (5:95 $Et_2O$: pentane) to yield a colorless oil (1.58 g, 76% yield).

$^1$H NMR (400 MHz, $CDCl_3$) δ 5.79 (ddt, J=16.9, 10.2, 6.7 Hz, 1H), 5.49 (dddd, J=10.7, 8.2, 6.7, 5.2 Hz, 1H), 5.42-5.29 (m, 1H), 4.99 (dq, J=17.1, 1.7 Hz, 1H), 4.93 (ddt, J=10.2, 2.3, 1.2 Hz, 1H), 4.06 (t, J=6.6 Hz, 2H), 2.30 (t, J=7.5 Hz, 2H), 2.16-1.98 (m, 4H), 1.73-1.55 (m, 7H), 1.46-1.28 (m, 4H).

$^{13}$C NMR (101 MHz, $CDCl_3$) b 174.00, 138.94, 129.24, 125.03, 114.53, 63.89, 34.45, 33.70, 28.74, 28.66, 28.56, 24.98, 23.31, 12.85.

HRMS (FAB+): [M]$^+$ $C_{14}H_{24}O_2$ Calculated—224.1776, Found—224.1745.

Example 2

Synthesis of (Z)-hex-3-en-1-yl dec-9-enoate (7)

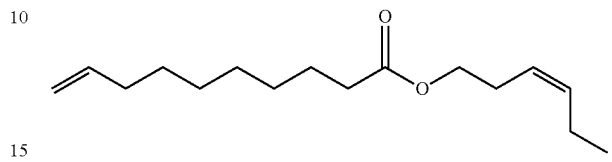

To a 100 mL round-bottom flask charged with a stir bar were added dichloromethane (50 mL), 9-decenoic acid (1.85 mL, 10.0 mmol), and pyridine (80.7 μL, 1.00 mmol). Oxalyl chloride (1.00 mL, 11.8 mmol) was added dropwise, and the reaction was stirred for overnight. The solvents were removed under vacuum. Dichloromethane (20 mL) and pyridine (0.81 mL, 10.0 mmol) were added, subsequently, cis-3-hexenol (1.10 mL, 9.3 mmol) was added dropwise at 0° C. After bringing the reaction to room temperature, it was stirred for an additional 4 h. The reaction mixture was extracted with 1M aq. HCl (200 mL) and sat. aq. $NaHCO_3$ (200 mL). The organic layer was dried over anhydrous $MgSO_4$, filtered, and the solvents were removed under vacuum. The product was purified by column chromatography on silica gel (5:95 $Et_2O$: pentane) to yield a colorless oil (2.02 g, 86% yield).

$^1$H NMR (400 MHz, $CDCl_3$) δ 5.79 (ddt, J=16.9, 10.2, 6.7 Hz, 1H), 5.64-5.37 (m, 1H), 5.37-5.14 (m, 1H), 5.02-4.94 (m, 1H), 4.92 (ddt, J=10.2, 2.3, 1.2 Hz, 1H), 4.05 (t, J=6.9 Hz, 2H), 2.43-2.32 (m, 2H), 2.28 (t, J=7.5 Hz, 2H), 2.12-1.89 (m, 4H), 1.67-1.50 (m, 2H), 1.42-1.19 (m, 8H), 0.96 (t, J=7.5 Hz, 3H).

$^{13}$C NMR (101 MHz, $CDCl_3$) δ 174.01, 139.22, 134.61, 123.90, 114.31, 63.88, 34.46, 33.89, 29.23, 29.21, 29.04, 28.97, 26.89, 25.07, 20.73, 14.37.

HRMS (FAB+): [M]$^+$ $C_{17}H_{30}O_2$ Calculated—266.2246, Found—266.2216.

Example 3

Synthesis of (Z)-hex-3-en-1-yl undec-10-enoate (8)

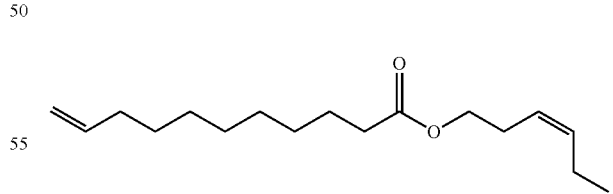

To a 100 mL round-bottom flask charged with a stir bar were added dichloromethane (20 mL), undecenoyl chloride (2.37 mL, 11.0 mmol), and pyridine (0.89 mL, 11.0 mmol). Cis-3-hexenol (1.18 mL, 10.0 mmol) was then added dropwise at 0° C. The reaction mixture was brought to room temperature and stirred for 4 h. The reaction mixture was extracted with 1M aq. HCl (200 mL) and sat. aq. $NaHCO_3$ (200 mL). The organic layer was dried over anhydrous $MgSO_4$, filtered, and the solvents were removed under vacuum. The product was purified by column chromatography on silica gel (5:95 Et$_2$O: pentane) to yield a colorless oil (2.53 g, 95% yield).

$^1$H NMR (400 MHz, CDCl$_3$) δ 5.80 (ddt, J=16.9, 10.2, 6.7 Hz, 1H), 5.55-5.45 (m, 1H), 5.36-5.26 (m, 1H), 4.99 (dq, J=17.1, 1.7 Hz, 1H), 4.92 (ddt, J=10.2, 2.3, 1.2 Hz, 1H), 4.06 (t, J=6.9 Hz, 2H), 2.43-2.31 (m, 2H), 2.32-2.24 (m, 2H), 2.04 (dddd, J=14.8, 7.9, 5.0, 1.5 Hz, 4H), 1.67-1.54 (m, 2H), 1.42-1.33 (m, 2H), 1.33-1.24 (m, 8H), 0.97 (t, J=7.5 Hz, 3H).

$^{13}$C NMR (101 MHz, CDCl$_3$) δ 174.06, 139.32, 134.63, 123.92, 114.28, 63.89, 34.49, 33.94, 29.43, 29.35, 29.26, 29.20, 29.04, 26.90, 25.11, 20.75, 14.39.

HRMS (FAB+): [M]$^+$ C$_{17}$H$_{30}$O$_2$ Calculated—266.2246, Found—266.2216.

Example 4

Synthesis of (Z)-hex-4-en-1-yl dec-9-enoate (9)

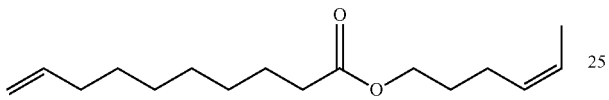

To a 100 mL round-bottom flask charged with a stir bar were added dichloromethane (50 mL), 9-decenoic acid (1.85 mL, 10.0 mmol), and pyridine (80.7 µL, 1.00 mmol). Oxalyl chloride (1.00 mL, 11.8 mmol) was added dropwise, and the reaction was stirred overnight. The solvents were removed under vacuum. Dichloromethane (20 mL) and pyridine (0.81 mL, 10.0 mmol) were added, subsequently, cis-4-hexenol (1.09 mL, 9.3 mmol) was added dropwise at 0° C. After bringing the reaction to room temperature, it was stirred for an additional 4 h. The reaction mixture was extracted with 1M aq. HCl (200 mL) and sat. aq. NaHCO$_3$ (200 mL). The organic layer was dried over anhydrous MgSO$_4$, filtered, and the solvents were removed under vacuum. The product was purified by column chromatography on silica gel (5:95 Et$_2$O: pentane) to yield a colorless oil (2.05 g, 87% yield).

$^1$H NMR (400 MHz, CDCl$_3$) δ 5.80 (ddt, J=13.2, 10.0, 7.2 Hz, 1H), 5.60-5.44 (m, 1H), 5.44-5.32 (m, 1H), 5.12-4.96 (m, 1H), 4.93 (ddd, J=10.2, 2.3, 1.2 Hz, 1H), 4.07 (t, J=6.5 Hz, 2H), 2.30 (t, J=8.0 Hz, 2H), 2.20-1.96 (m, 4H), 1.81-1.58 (m, 7H), 1.49-1.24 (m, 8H).

$^{13}$C NMR (101 MHz, CDCl$_3$) b 174.12, 139.29, 129.27, 125.05, 114.34, 63.89, 34.53, 33.92, 29.26, 29.07, 29.00, 28.59, 25.14, 23.34, 12.88.

HRMS (FAB+): [M+H] C$_{16}$H$_{29}$O$_2$ Calculated—253.2158, Found—253.2168.

Example 5

Synthesis of (Z)-hex-4-en-1-yl undec-10-enoate (10)

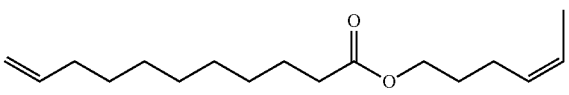 [SMILES: C=CCCCCCCCCC(=O)OCCC/C=C\C]

To a 100 mL round-bottom flask charged with a stir bar were added dichloromethane (20 mL), undecenoyl chloride (2.37 mL, 11.0 mmol), and pyridine (0.89 mL, 11.0 mmol). Cis-4-hexenol (1.17 mL, 10.0 mmol) was added dropwise at 0° C. The reaction mixture was brought to room temperature and stirred for 4 h. The reaction mixture was extracted with 1M aq. HCl (200 mL) and sat. aq. NaHCO$_3$ (200 mL). The organic layer was dried over anhydrous MgSO$_4$, filtered, and the solvents were removed under vacuum. The product was purified by column chromatography on silica gel (5:95 Et$_2$O: pentane) to yield a colorless oil (2.45 g, 92% yield).

$^1$H NMR (400 MHz, CDCl$_3$) δ 5.80 (ddt, J=16.9, 10.2, 6.7 Hz, 1H), 5.49 (dddd, J=10.7, 8.2, 6.7, 5.2 Hz, 1H), 5.36 (dtq, J=10.7, 7.3, 1.7 Hz, 1H), 4.99 (dq, J=17.2, 1.8 Hz, 1H), 4.92 (ddt, J=10.2, 2.3, 1.2 Hz, 1H), 4.06 (t, J=6.6 Hz, 2H), 2.29 (t, J=7.5 Hz, 2H), 2.11 (qt, J=7.2, 1.2 Hz, 2H), 2.07-1.99 (m, 2H), 1.73-1.64 (m, 2H), 1.60 (ddt, J=6.7, 1.8, 0.9 Hz, 6H), 1.36 (dt, J=8.3, 4.8 Hz, 2H), 1.28 (q, J=4.1, 3.3 Hz, 7H).

$^{13}$C NMR (101 MHz, CDCl$_3$) b 174.12, 139.33, 129.26, 125.04, 114.28, 63.89, 34.54, 33.94, 29.44, 29.36, 29.28, 29.21, 29.04, 28.58, 25.15, 23.33, 12.86.

HRMS (FAB+): [M+H] C$_{17}$H$_{31}$O$_2$ Calculated—267.2324, Found—267.2335.

Example 6

Synthesis of (Z)-oct-5-en-1-yl undec-10-enoate (11)

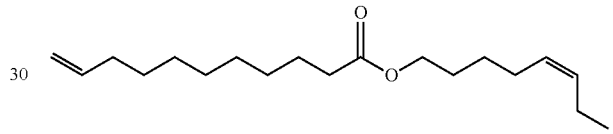

To a 100 mL round-bottom flask charged with a stir bar were added dichloromethane (20 mL), undecenoyl chloride (2.37 mL, 11.0 mmol), and pyridine (0.89 mL, 11.0 mmol). Cis-5-octenol (1.51 mL, 10.0 mmol) was added dropwise at 0° C.; the reaction mixture was brought to room temperature and stirred for 4 h. The reaction mixture was extracted with 1M aq. HCl (200 mL) and sat. aq. NaHCO$_3$ (200 mL). The organic layer was dried over anhydrous MgSO$_4$, filtered, and the solvents were removed under vacuum. The product was purified by column chromatography on silica gel (5:95 Et$_2$O: pentane) to yield a colorless oil (2.82 g, 96% yield).

$^1$H NMR (400 MHz, CDCl$_3$) δ 5.82 (ddt, J=16.9, 10.1, 6.7 Hz, 1H), 5.46-5.37 (m, 1H), 5.36-5.25 (m, 1H), 5.01 (dq, J=17.1, 1.8 Hz, 1H), 4.94 (ddt, J=10.2, 2.4, 1.2 Hz, 1H), 4.08 (t, J=6.7 Hz, 2H), 2.31 (t, J=7.6 Hz, 2H), 2.06 (dddd, J=10.9, 9.5, 5.3, 1.6 Hz, 6H), 1.72-1.61 (m, 4H), 1.47-1.27 (m, 12H), 0.97 (t, J=7.5 Hz, 3H).

$^{13}$C NMR (101 MHz, CDCl$_3$) δ 173.99, 139.17, 132.16, 128.49, 114.14, 64.22, 34.39, 33.80, 29.31, 29.22, 29.14, 29.07, 28.90, 28.23, 26.63, 26.05, 25.02, 20.54, 14.36.

HRMS (FAB+): [M+H] C$_{19}$H$_{35}$O$_2$ Calculated—295.2637, Found—295.2639.

Example 7

Synthesis (Z)-non-6-en-1-yl undec-10-enoate (12)

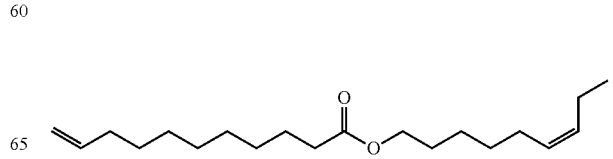

To a 100 mL round-bottom flask charged with a stir bar were added dichloromethane (20 mL), undecenoyl chloride (2.37 mL, 11.0 mmol), and pyridine (0.89 mL, 11.0 mmol). Cis-6-nonenol (1.67 mL, 10.0 mmol) was then added dropwise at 0° C. The reaction mixture was brought to room temperature and stirred for 4 h. The reaction mixture was extracted with 1M aq. HCl (200 mL) and sat. aq. NaHCO$_3$ (200 mL). The organic layer was dried over anhydrous MgSO$_4$, filtered, and the solvents were removed under vacuum. The product was purified by column chromatography on silica gel (5:95 Et$_2$O: pentane) to yield a colorless oil (2.74 g, 89% yield).

$^1$H NMR (400 MHz, CDCl$_3$) δ 5.80 (ddt, J=16.9, 10.2, 6.7 Hz, 1H), 5.50-5.16 (m, 2H), 5.04-4.94 (m, 1H), 4.94-4.88 (m, 1H), 4.05 (t, J=6.7 Hz, 2H), 2.35-2.22 (m, 2H), 2.13-1.96 (m, 6H), 1.61 (dt, J=11.8, 4.1 Hz, 4H), 1.36 (dt, J=6.5, 2.2 Hz, 6H), 1.32-1.25 (m, 8H), 0.95 (t, J=7.5 Hz, 3H).

$^{13}$C NMR (101 MHz, CDCl$_3$) δ 174.14, 139.32, 131.99, 128.96, 114.28, 64.47, 34.54, 33.94, 29.48, 29.44, 29.36, 29.28, 29.21, 29.03, 28.70, 27.07, 25.70, 25.15, 20.66, 14.52.

HRMS (FAB+): [M]$^+$ C$_{20}$H$_{37}$O$_2$ Calculated—309.2794, Found—309.2779.

Synthesis of Z-Macrocyclic products

Example 8

Synthesis of (Z)-oxacyclododec-8-en-2-one (Z-6)

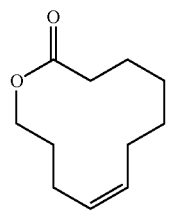 [SMILES: O=C1CCCCC/C=C\CCCO1]

To a 150 mL Schlenk tube equipped with a stir bar were added diene (6) (21.0 mg, 0.0938 mmol) in DCM (30.3 mL) and a solution of catalyst 5 (4.8 mg, 0.00563 mmol) in DCM (1 mL). The tube was sealed and taken out of the glovebox. After one freeze, pump, thaw cycle, the reaction flask was heated at 40° C. for 1 h and quenched with butyl vinyl ether (1 mL). The solvents were removed under vacuum, and the product was purified by column chromatography on silica gel (1:49 Et$_2$O: pentane) to yield a colorless oil (12.0 mg, 70% yield).

$^1$H NMR (400 MHz, CDCl$_3$) δ 5.45-5.21 (m, 2H), 4.10-3.96 (m, 2H), 2.49-2.28 (m, 4H), 2.18 (q, J=6.3 Hz, 2H), 1.89-1.81 (m, 2H), 1.68 (ddq, J=8.2, 4.0, 2.0 Hz, 2H), 1.47-1.40 (m, 2H), 1.26-1.18 (m, 2H).

$^{13}$C NMR (101 MHz, CDCl$_3$) b 174.18, 131.37, 128.57, 62.31, 35.73, 26.80, 26.30, 25.14, 24.18, 23.08, 22.42.

HRMS (FAB+): [M]$^+$ C$_{11}$H$_{18}$O$_2$ Calculated—182.1307, Found—182.1303.

Example 9

Synthesis of (Z)-oxacyclotridec-10-en-2-one (Z-7)

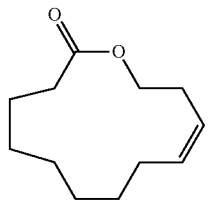 [SMILES: O=C1CCCCCCC/C=C\CCO1]

To a 150 mL Schlenk tube equipped with a stir bar were added diene (7) (23.7 mg, 0.0938 mmol) in DCM (30.3 mL) and a solution of catalyst 5 (4.8 mg, 0.00563 mmol) in DCM (1 mL). The tube was sealed and taken out of the glovebox. After one freeze, pump, thaw cycle, the reaction flask was heated at 40° C. for 1 h and quenched with butyl vinyl ether (1 mL). The solvents were removed under vacuum, and the product was purified by column chromatography on silica gel (1:49 Et$_2$O: pentane) to yield a colorless oil (12.5 mg, 68% yield).

$^1$H NMR (400 MHz, CDCl$_3$) δ 5.50-5.32 (m, 2H), 4.30-4.15 (m, 2H), 2.43 (q, J=5.0 Hz, 2H), 2.35-2.25 (m, 2H), 2.15-2.04 (m, 2H), 1.73-1.64 (m, 2H), 1.49 (q, J=6.3 Hz, 2H), 1.41-1.33 (m, 2H), 1.22-1.15 (m, 2H).

$^{13}$C NMR (101 MHz, CDCl$_3$) b 174.89, 132.41, 127.26, 64.34, 35.54, 29.86, 27.66, 27.41, 26.15, 26.02, 24.73, 23.67.

HRMS (EI): C$_{12}$H$_{21}$O$_2$ Calculated—197.1542, Found—197.1536.

Example 10

Synthesis of (Z)-oxacyclotetradec-11-en-2-one (Z-8)

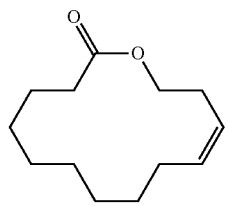 [SMILES: O=C1CCCCCCCC/C=C\CCO1]

To a 150 mL Schlenk tube equipped with a stir bar were added diene (8) (25.0 mg, 0.0938 mmol) in DCM (30.3 mL) and a solution of catalyst 5 (4.8 mg, 0.00563 mmol) in DCM (1 mL). The tube was sealed and taken out of the glovebox. After one freeze, pump, thaw cycle, the reaction flask was heated at 40° C. for 1 h and quenched with butyl vinyl ether (1 mL). The solvents were removed under vacuum, and the product was purified by column chromatography on silica gel (1:49 Et$_2$O: pentane) to yield a colorless oil (13.2 mg, 67% yield).

$^1$H NMR (400 MHz, CDCl$_3$) δ 5.55 (dtt, J=11.1, 7.7, 1.7 Hz, 1H), 5.45-5.33 (m, 1H), 4.28-4.11 (m, 2H), 2.50-2.40 (m, 2H), 2.40-2.29 (m, 2H), 2.10-1.99 (m, 2H), 1.66 (ddt, J=6.3, 4.5, 2.5 Hz, 2H), 1.43-1.30 (m, 10H).

$^{13}$C NMR (101 MHz, CDCl$_3$) δ 174.13, 132.47, 127.22, 63.89, 33.46, 27.85, 27.65, 26.25, 26.14, 25.67, 25.56, 25.34, 23.65.

HRMS (FAB+): [M+H] C$_{13}$H$_{23}$O$_2$ Calculated—211.1698, Found—211.1706.

Example 11

Synthesis of (Z)-oxacyclotetradec-10-en-2-one (Z-9)

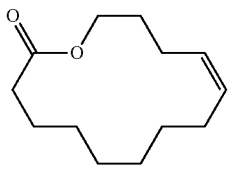 [SMILES: O=C1CCCCCCC/C=C\CCCO1]

To a 150 mL Schlenk tube equipped with a stir bar were added a solution of diene (9) (23.7 mg, 0.0938 mmol) in DCM (30.3 mL) and a solution of catalyst 5 (4.8 mg, 0.00563 mmol) in DCM (1 mL). The tube was sealed and taken out of the glovebox. After one freeze, pump, thaw cycle, the reaction flask was heated at 40° C. for 1 h and then quenched with butyl vinyl ether (1 mL). The solvents were removed under vacuum, and the product was purified by column chromatography on silica gel (1:49 Et$_2$O: pentane) to yield a colorless oil (14.2 mg, 72% yield).

$^1$H NMR (400 MHz, CDCl$_3$) δ 5.48 (dtt, J=10.5, 7.6, 1.5 Hz, 1H), 5.33 (dtt, J=10.5, 7.6, 1.3 Hz, 1H), 4.22-4.02 (m, 2H), 2.51-2.37 (m, 2H), 2.25 (qd, J=7.5, 1.4 Hz, 2H), 2.14-1.95 (m, 2H), 1.79-1.65 (m, 4H), 1.49-1.28 (m, 8H).

$^{13}$C NMR (101 MHz, CDCl$_3$) b 173.98, 131.23, 128.50, 62.84, 33.57, 29.11, 27.00, 26.77, 26.03, 25.23, 25.04, 24.63, 23.73.

HRMS (FAB+): [M+H] C$_{13}$H$_{23}$O$_2$ Calculated—211.1698, Found—211.1690.

Example 12

Synthesis of (Z)-oxacyclopentadec-11-en-2-one (Z-10)

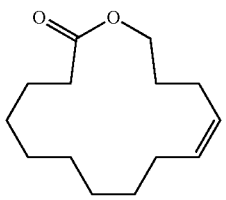 [SMILES: O=C1CCCCCCCC/C=C\CCCO1]

To a 150 mL Schlenk tube equipped with a stir bar were added a solution of diene (10) (25.0 mg, 0.0938 mmol) in DCM (30.3 mL) and a solution of catalyst 5 (4.8 mg, 0.00563 mmol) in DCM (1 mL). The tube was sealed and taken out of the glovebox. After one freeze, pump, thaw cycle, the reaction flask was heated at 40° C. for 1 h and quenched with butyl vinyl ether (1 mL). The solvents were removed under vacuum, and the product was purified by column chromatography on silica gel (1:49 Et$_2$O: pentane) to yield a colorless oil (15.6 mg, 70% yield).

$^1$H NMR (400 MHz, CDCl$_3$) δ 5.57-5.38 (m, 1H), 5.30 (dt, J=10.9, 6.9 Hz, 1H), 4.18-3.95 (m, 2H), 2.46-2.32 (m, 2H), 2.23 (qd, J=7.1, 1.7 Hz, 2H), 2.02 (q, J=7.1 Hz, 2H), 1.72 (dtd, J=8.9, 6.9, 4.3 Hz, 4H), 1.36 (dt, J=8.7, 5.9 Hz, 10H).

$^{13}$C NMR (101 MHz, CDCl$_3$) b 174.45, 131.47, 128.85, 63.36, 34.51, 28.81, 28.24, 27.96, 27.12, 27.05, 27.01, 26.35, 24.63, 23.75.

HRMS (FAB+): [M]$^+$ C$_{14}$H$_{24}$O$_2$ Calculated—224.1776, Found—224.1774.

Example 13

Synthesis of (Z)-oxacyclohexadec-11-en-2-one (Z-11)

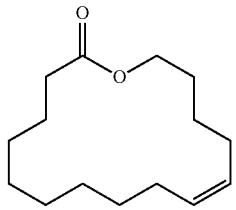 [SMILES: O=C1CCCCCCCC/C=C\CCCCO1]

To a 150 mL Schlenk tube equipped with a stir bar were added a solution of diene (11) (27.6 mg, 0.0938 mmol) in DCM (30.3 mL) and a solution of catalyst 5 (4.8 mg, 0.00563 mmol) in DCM (1 mL). The tube was sealed and taken out of the glovebox. After one freeze, pump, thaw cycle, the reaction flask was heated at 40° C. for 1 h and quenched with butyl vinyl ether (1 mL). Solvents were removed under vacuum, and the product was purified by column chromatography on silica gel (1:49 Et$_2$O: pentane) to yield a colorless oil (17.7 mg, 79% yield).

$^1$H NMR (400 MHz, CDCl$_3$) δ 5.53-5.20 (m, 2H), 4.14 (t, J=6.3 Hz, 2H), 2.43-2.27 (m, 2H), 2.03 (qd, J=7.0, 3.1 Hz, 4H), 1.63 (dq, J=9.2, 6.3 Hz, 4H), 1.45-1.37 (m, 2H), 1.30 (q, J=5.5, 4.6 Hz, 10H).

$^{13}$C NMR (101 MHz, CDCl$_3$) δ 174.09, 130.24, 129.71, 64.24, 34.01, 29.28, 28.54, 28.31, 28.07, 27.76, 27.32, 27.25, 26.73, 26.61, 25.38.

HRMS (FAB+): [M+H] C$_{15}$H$_{27}$O$_2$ Calculated—239.2011, Found—239.2017.

Example 14

Synthesis of (Z)-oxacycloheptadec-11-en-2-one (Z-12)

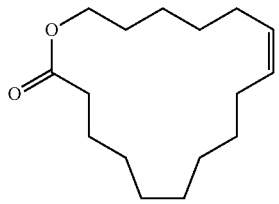 [SMILES: O=C1CCCCCCCC/C=C\CCCCCO1]

To a 150 mL Schlenk tube equipped with a stir bar were added a solution of diene (12) (28.9 mg, 0.0938 mmol) in DCM (30.3 mL) and a solution of catalyst 5 (4.8 mg, 0.00563 mmol) in DCM (1 mL). The tube was sealed and taken out of the glovebox. After one freeze, pump, thaw cycle, the reaction flask was heated at 40° C. for 1 h and quenched with butyl vinyl ether (1 mL). The solvents were removed under vacuum, and the product was purified by column chromatography on silica gel (1:49 Et$_2$O: pentane) to yield a colorless oil (17.8 mg, 75% yield).

$^1$H NMR (400 MHz, CDCl$_3$) δ 5.39-5.22 (m, 2H), 4.19-4.01 (m, 2H), 2.38-2.22 (m, 2H), 2.06 (dq, J=18.6, 6.1 Hz, 4H), 1.71-1.52 (m, 4H), 1.47-1.17 (m, 14H).

$^{13}$C NMR (101 MHz, CDCl$_3$) b 174.57, 130.37, 130.29, 64.75, 34.43, 29.45, 28.88, 28.84, 28.79, 28.76, 28.19, 27.73, 27.32, 26.57, 26.22, 25.57.

HRMS (FAB+): [M+H] C$_{16}$H$_{28}$O$_2$ Calculated—252.2087, Found—252.2089.

Synthesis of E/Z-Macrocyclic Products

For determining the selectivity of the synthesized Z-macrocyclic products, E/Z mixtures of unsaturated lactones were synthesized using catalyst C823 (PCy$_3$)$_2$Cl$_2$Ru=CHPh as references for GC and $^{13}$C NMR studies for comparison.

Example 15

Synthesis of (E/Z)-oxacyclotetradec-10-en-2-one (E/Z-9)

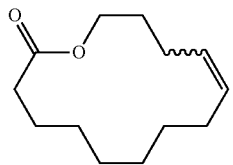 [SMILES: O=C1CCCCCCCC=CCCCO1]

To a 150 mL Schlenk tube equipped with a stir bar were added a solution of diene (9) (23.7 mg, 0.0938 mmol) in DCM (30.3 mL) and a solution of catalyst C823 (4.6 mg, 0.00563 mmol) in DCM (1 mL). The tube was sealed and taken out of the glovebox. After one freeze, pump, thaw cycle, the reaction flask was heated at 40° C. for 4 h and quenched with butyl vinyl ether (1 mL). The solvents were removed under vacuum, and the product was purified by column chromatography on silica gel (1:49 Et$_2$O: pentane) to yield a colorless oil (13.0 mg, 67% yield).

$^1$H NMR (400 MHz, CDCl$_3$) δ 5.68-5.42 (m, 1H), 5.42-5.24 (m, 1H), 4.29-3.98 (m, 2H), 2.53-2.18 (m, 4H), 2.14-2.05 (m, 2H), 1.79-1.64 (m, 4H), 1.49-1.20 (m, 12H).

$^{13}$C NMR (101 MHz, CDCl$_3$) δ 174.28, 173.86, 131.11, 130.62, 130.40, 128.38, 64.81, 62.72, 33.45, 33.01, 31.42, 30.91, 28.98, 28.18, 27.06, 26.88, 26.65, 26.53, 25.91, 25.11, 24.98, 24.92, 24.51, 24.08, 23.61.

HRMS (FAB+): [M]$^+$ C$_{13}$H$_{22}$O$_2$ Calculated—210.1620, Found—210.1633.

Example 16

Synthesis of (E/Z)-oxacyclopentadec-11-en-2-one (E/Z –10)

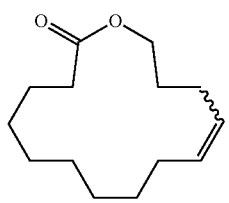 [SMILES: O=C1CCCCCCCCC=CCCCO1]

To a 150 mL Schlenk tube equipped with a stir bar were added a solution of diene (10) (25.0 mg, 0.0938 mmol) in DCM (30.3 mL) and a solution of catalyst C823 (4.6 mg, 0.00563 mmol) in DCM (1 mL). The tube was sealed and taken out of the glovebox. After one freeze, pump, thaw cycle, the reaction flask was heated at 40° C. for 4 h and quenched with 1 mL butyl vinyl ether (1 mL). The solvents were removed under vacuum, and the product was purified by column chromatography on silica gel (1:49 Et$_2$O: pentane) to yield a colorless oil (11.7 mg, 52% yield).

$^1$H NMR (400 MHz, CDCl$_3$) δ 5.50-5.20 (m, 2H), 4.19-4.04 (m, 2H), 2.40-2.29 (m, 2H), 2.20 (qd, J=7.4, 6.3, 1.6 Hz, 2H), 2.09-1.96 (m, 2H), 1.85-1.54 (m, 5H), 1.45-1.22 (m, 11H).

$^{13}$C NMR (101 MHz, CDCl$_3$) b 174.48, 174.45, 131.97, 131.48, 129.87, 128.85, 64.30, 63.36, 35.01, 34.51, 31.02, 30.32, 28.81, 28.24, 27.96, 27.85, 27.56, 27.13, 27.05, 27.03, 27.01, 26.82, 26.63, 26.35, 25.03, 24.63, 24.57, 23.75.

HRMS (FAB+): [M]$^+$ C$_{14}$H$_{24}$O$_2$ Calculated—224.1776, Found—224.1767.

Example 17

Synthesis of (E/Z)-oxacyclohexadec-11-en-2-one (E/Z-11)

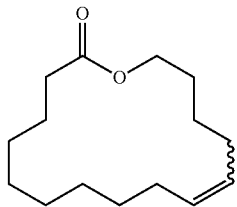 [SMILES: O=C1CCCCCCCCC=CCCCCO1]

To a 150 mL Schlenk tube equipped with a stir bar were added a solution of diene (11) (27.6 mg, 0.0938 mmol) in DCM (30 mL) and a solution of catalyst C823 (4.6 mg, 0.00563 mmol) in DCM (1 mL). The tube was sealed and taken out of the glovebox. After one freeze, pump, thaw cycle, the reaction flask was heated at 40° C. for 4 h and quenched with butyl vinyl ether (1 mL). The solvents were removed under vacuum, and the product was purified by column chromatography on silica gel (1:49 Et$_2$O: pentane) to yield a colorless oil (16.8 mg, 75% yield).

$^1$H NMR (400 MHz, CDCl$_3$) δ 5.52-5.15 (m, 2H), 4.22-4.01 (m, 2H), 2.45-2.22 (m, 2H), 2.03 (ddt, J=9.1, 6.8, 3.8 Hz, 4H), 1.61 (dtd, J=15.7, 7.1, 4.0 Hz, 4H), 1.42-1.11 (m, 12H).

$^{13}$C NMR (101 MHz, CDCl$_3$) b 174.09, 174.07, 131.95, 130.46, 130.24, 129.71, 64.24, 64.08, 34.89, 34.01, 32.16, 32.12, 29.28, 28.54, 28.47, 28.41, 28.34, 28.31, 28.14, 28.07, 27.76, 27.34, 27.32, 27.25, 26.73, 26.68, 26.61, 25.60, 25.38, 25.30.

HRMS (FAB+): [M]$^+$ C$_{15}$H$_{26}$O$_2$ Calculated—238.1933, Found—238.1926.

Example 18

Synthesis of (E/Z)-oxacycloheptadec-11-en-2-one (E/Z –12)

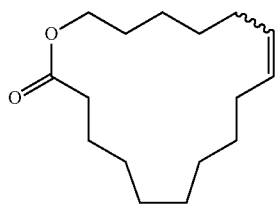 [SMILES: O=C1CCCCCCCCC=CCCCCCO1]

To a 150 mL Schlenk tube equipped with a stir bar were added a solution of diene (12) (28.9 mg, 0.0938 mmol) in DCM (30.3 mL) and a solution of catalyst C823 (4.6 mg, 0.00563 mmol) in DCM (1 mL). The tube was sealed and taken out of the glovebox. After one freeze, pump, thaw cycle, the reaction flask was heated at 40° C. for 4 h and quenched with butyl vinyl ether (1 mL). The solvents were removed under vacuum, and the product was purified by column chromatography on silica gel (1:49 Et$_2$O: pentane) to yield a colorless oil (16.4 mg, 69% yield).

$^1$H NMR (400 MHz, CDCl$_3$) δ 5.39-5.22 (m, 2H), 4.19-4.02 (m, 2H), 2.40-2.25 (m, 2H), 2.04 (ddt, J=14.3, 11.9, 4.8 Hz, 4H), 1.68-1.56 (m, 4H), 1.48-1.22 (m, 14H).

$^{13}$C NMR (101 MHz, CDCl$_3$) δ 173.38, 129.79, 129.71, 129.18, 129.10, 63.87, 63.56, 33.64, 33.24, 31.57, 30.70, 28.66, 28.26, 28.19, 28.14, 27.71, 27.68, 27.65, 27.60, 27.57, 27.38, 27.14, 27.00, 26.94, 26.91, 26.54, 26.13, 25.93, 25.38, 25.02, 24.96, 24.38, 24.30, 24.28.

HRMS (FAB+): [M]$^+$ C$_{16}$H$_{28}$O$_2$ Calculated—252.2079, Found—252.2089.

General Procedure for Catalyst Initiation Experiments

A solution of catalyst (0.003 mmol) in CD$_2$Cl$_2$ (0.6 mL) was added to a NMR tube and the tube was sealed with a rubber septum. The tube was taken out of the glovebox and placed in a dry ice/acetone bath. Butyl vinyl ether (12 μL, 0.090 mmol) was injected into the tube, and the reaction was monitored by observing the disappearance of the benzylidene signal by $^1$H NMR using an array at the appropriate temperature. FIG. 4 captures the results.

What is claimed is:

1. A method for producing at least one Z-macrocyclic product represented by Formula (VII):

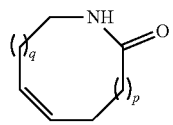

Formula (VII)

wherein:
q is 1, 2, 3, or 4; p is 4, 5, 6, or 7; and the Z-macrocyclic product of Formula (VII) is a twelve, thirteen, fourteen, fifteen, sixteen, or seventeen-membered ring with a Z selectivity of 95, or 98, or 99; comprising:

subjecting a diene substrate bearing a Z-olefin moiety represented by Formula (IV):

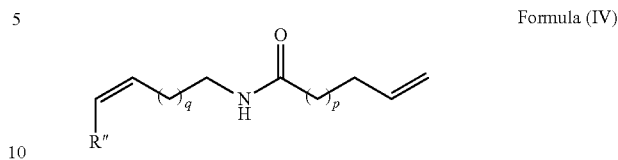

Formula (IV)

wherein:
R″ is methyl, ethyl, or propyl; q is 1, 2, 3, or 4; p is 4, 5, 6, or 7;

to a macrocyclic ring-closing metathesis reaction in the presence of a stereoretentive Ru-based catalyst represented by Formula (II):

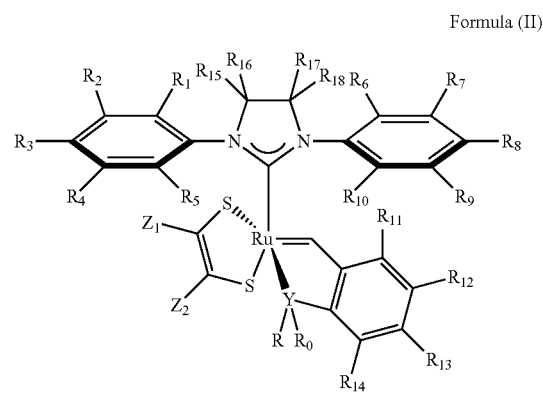

Formula (II)

wherein:
R and R$_0$ are independently nil, H, methyl, ethyl, propyl, iso-propyl, butyl, sec-butyl, tert-butyl, or phenyl;

R$_1$, R$_2$, R$_3$, R$_4$, R$_5$, R$_6$, R$_7$, R$_8$, R$_9$, R$_{10}$, R$_{11}$, R$_{12}$, R$_{13}$, and R$_{14}$ are independently H, methyl, ethyl, propyl, iso-propyl, butyl, sec-butyl, tert-butyl, phenyl, fluoro, chloro, bromo, iodo, nitro, dimethylaminosulfonate, diethylaminosulfonate, or cyano;

R$_{15}$, R$_{16}$, R$_{17}$, and R$_{18}$ are independently H or methyl;

Z$_1$ and Z$_2$ are independently cyano or nitro; and

Y is oxygen, sulfur, nitrogen, or iodo.

2. The method of claim 1, wherein the stereoretentive Ru-based catalyst represented by Formula (II) is selected from the group consisting of:

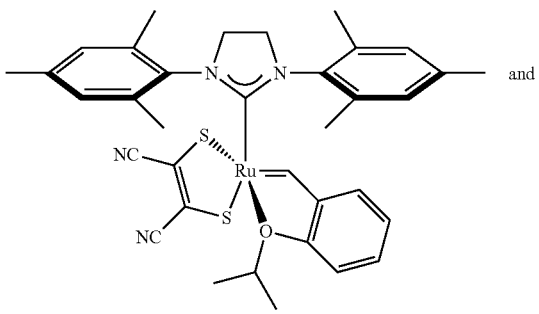

C696cn and

-continued
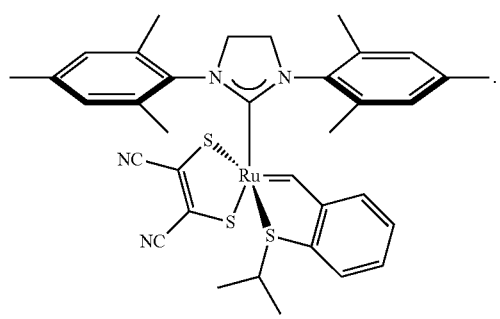
C712
* * * * *